US005817700A

United States Patent [19]

Dube et al.

[11] Patent Number: 5,817,700

[45] Date of Patent: Oct. 6, 1998

[54] BISARYL CYCLOBUTENES DERIVATIVES AS CYCLOOXYGENASE INHIBITORS

[75] Inventors: Daniel Dube, St. Lazare; Rejean Fortin, Montreal-Nord; Richard Frenette, Vimont; Richard Friesen, Dollard Des Ormeaux; Daniel Guay, Ile Perrot; Sylvie Prescott, Chomedey, all of Canada

[73] Assignee: Merck Frosst Canada, Inc., Kirkland, Canada

[21] Appl. No.: 814,388

[22] Filed: Mar. 11, 1997

Related U.S. Application Data

[60] Provisional application No. 60/014,287 Mar. 29, 1996.

[51] Int. Cl.[6] .......................... A61K 31/10; C07C 317/10

[52] U.S. Cl. .............................................. 514/768; 568/31

[58] Field of Search ............................... 568/31; 514/768

[56] References Cited

U.S. PATENT DOCUMENTS

| | | | |
|---|---|---|---|
| 3,335,195 | 8/1967 | Freedman et al. | 260/649 |
| 4,967,002 | 10/1990 | Pain | 564/307 |
| 5,077,142 | 12/1991 | Sakon et al. | 428/690 |

FOREIGN PATENT DOCUMENTS

| | | |
|---|---|---|
| 0 313 942 | 10/1988 | European Pat. Off. . |
| 2046068 | 2/1971 | France . |
| 05117218 | 5/1993 | Japan . |
| WO 95/34556 | 12/1995 | WIPO . |

OTHER PUBLICATIONS

Lawson, et al, Journal of Medicinal Chemistry, vol. 17, No. 4, Apr. 1974 "Diarylcyclobutane Analogs of Diethylstilbestrol" pp. 383–386.

Friesen, R.W. et al.: Novel 1,2–diaxylcyclobutenes Selective and orally active CoX–2 inhibitors.

Bioorganic & Medicinal Chemistry Letters, vol. 6, No. 22, pp. 2677–2682, 1996.

Paull, K. D. et al. Cancer Res. vol. 52, No. 14, pp. 3892–3900 (1992).

*Primary Examiner*—Alan L. Rotman
*Assistant Examiner*—Charanjit S. Awlakh
*Attorney, Agent, or Firm*—Richard C. Billups; David L. Rose

[57] ABSTRACT

The invention encompasses the novel compound of Formula I useful in the treatment of cyclooxygenase-2 mediated diseases.

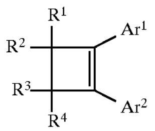

I

The invention also encompasses certain pharmaceutical compositions for treatment of cyclooxygenase-2 mediated diseases comprising compounds of Formula I.

21 Claims, No Drawings

BISARYL CYCLOBUTENES DERIVATIVES AS CYCLOOXYGENASE INHIBITORS

CROSS REFERENCE TO RELATED APPLICATION

This application is a non-provisional application based upon provisional application Ser. No. 60/014,287 filed on Mar. 29, 1996, which is claimed hereunder.

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 (COX-1) or the constitutive enzyme, as originally identified in bovine seminal vesicles. More recently the gene for a second inducible form of cyclooxygenase, cyclooxygenase-2 (COX-2) has been cloned, sequenced and characterized initially from chicken, murine and human sources. This enzyme is distinct from the COX- 1 which has been cloned, sequenced and characterized from various sources including the sheep, the mouse and man. The second form of cyclooxygenase, COX-2, is rapidly and readily inducible by a number of agents including mitogens, endotoxin, hormones, cytokines and growth factors. As prostaglandins have both physiological and pathological roles, we have concluded that the constitutive enzyme, COX-1, is responsible, in large part, for endogenous basal release of prostaglandins and hence is important in their physiological functions such as the maintenance of gastrointestinal integrity and renal blood flow. In contrast, we have concluded that the inducible form, COX-2, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Furthermore, such a compound will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease and for decreasing bone loss particularly in postmenopausal women (i.e. treatment of osteoporosis).

A brief description of the potential utility of cyclooxygenase-2 inhibitors is given in an article by John Vane, *Nature*, Vol. 367, pp. 215–216, 1994, and in an article in *Drug News and Perspectives*, Vol. 7, pp. 501–512, 1994.

SUMMARY OF THE INVENTION

The invention encompasses the novel compound of Formula I as well as a method of treating COX-2 mediated diseases comprising administration to a patient in need of such treatment of a non-toxic therapeutically effective amount of a compound of Formula I.

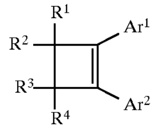

I

The invention also encompasses certain pharmaceutical compositions for treatment of COX-2 mediated diseases comprising compounds of Formula I.

DETAILED DESCRIPTION OF THE INVENTION

The invention encompasses the novel compound of Formula I as well as a method of treating COX-2 mediated diseases comprising administration to a patient in need of such treatment of a non-toxic therapeutically effective amount of a compound of Formula I.

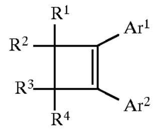

I wherein $R^1$, $R^2$, $R^3$ and $R^4$ is each independently H, halogen, hydroxy, alkyl, alkenyl, alkynyl, alkoxy, hydroxy alkyl, alkylthio, CN, $COR^5$, $OCOR^6$, $OCONHR^7$, $(R^{11})_{1-3}$-phenyl, $(R^{11})_{1-3}$-pyridyl, or is $(R^{11})_{1-3}$-arylene, wherein arylene is: a five membered aromatic ring containing one O,S or $NR^{14}$, with 0–2 carbon atoms replaced by N.

or $R^1$ and $R^2$ or $R^3$ and $R^4$ are joined together to form a double bonded oxygen (=O)

or $R^1$ and $R^2$ or $R^3$ and $R^4$ are joined together to form a double bonded sulfur (=S)

or $R^1$ and $R^2$ or $R^3$ and $R^4$ are joined together to form a double bonded substituted carbon atom ($=CR^8R^9$)

or $R^1$ and $R^2$ or $R^3$ and $R^4$ are joined together to form a double bonded substituted nitrogen atom ($=NR^{10}$)

or $R^1$ and $R^2$ or $R^3$ and $R^4$ are joined together to form a saturated monocyclic ring of 3,4,5,6 or 7 carbon atoms (spiro cycloalkyl)

or $R^1$ and $R^2$ or $R^3$ and $R^4$ are joined together to form a five or six membered saturated heterocyclic ring containing 1 or 2 heteroatoms chosen from oxygen, sulfur or $NR^{10}$, and optionally containing a carbonyl or a sulfonyl group;

$Ar^1$ is $(R)^{12}$-phenyl or $(R)^{12}$-naphthyl;

$Ar^2$ is $(R^{11})_{1-3}$-phenyl or $(R^{11})_{1-3}$-pyridyl, or is $(R^{11})_{1-3}$-arylene, wherein arylene is: a five membered aromatic ring containing one O,S or $NR^{14}$ with 0–2 carbon atoms replaced by N;

$R^5$ is H, alkyl, alkoxy;

$R^6$ is alkyl, alkoxy, $(R^{11})_{1-3}$-phenyl or $(R^{11})_{1-3}$-pyridyl;

$R^7$ is H, alkyl, $(R^{11})_{1-3}$-phenyl or $(R^{11})_{1-3}$-pyridyl;

$R^8$ and $R^9$ is each independently H, hydroxy alkyl, alkyl, CN, $COR^5$;

$R^{10}$ is hydroxy, alkoxy, alkyl, $(R^{11})_{1-3}$-phenylalkyl, $(R^{11})_{1-3}$-pyridylalkyl, $(R^{11})_{1-3}$-phenylalkoxy or $(R^{11})_{1-3}$-pyridylalkoxy;

$R^{11}$ is H, halogen, alkyl, hydroxy, hydroxy alkyl, alkoxy, $CF_3$, CN, $COR^5$, $S(O)_{0-2}R^{13}$;

$R^{12}$ is $S(O)_{0-2}R^{13}$, $S(O)_2NHR^{14}$ $R^{13}$ is alkyl;

$R^{14}$ is H, alkyl;

or a pharmaceutically acceptable salt thereof.

A preferred embodiment of the present invention is represented by Formula Ia:

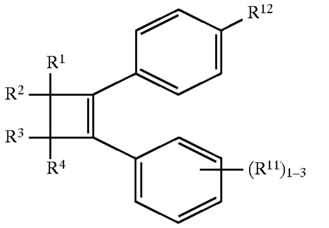

Ia $R^1$, $R^2$, $R^3$ and $R^4$ is each independently H, halogen, OH, alkyl, alkoxy, $OCOR^6$, $OCONHR^7$, $(R^{11})_{1-2}$-phenyl, or $(R^{11})_{1-2}$-arylene, wherein arylene is: a five membered aromatic ring containing one O, S or $NR^{14}$;

or $R^1$ and $R^2$ or $R^3$ and $R^4$ are joined together to form a double bonded oxygen (=O)

or $R^1$ and $R^2$ or $R^3$ and $R^4$ are joined together to form a double bonded substituted carbon atom ($=CR^8R^9$)

or $R^1$ and $R^2$ or $R^3$ and $R^4$ are joined together to form a double bonded substituted nitrogen atom ($=NR^{10}$)

or $R^1$ and $R^2$ or $R^3$ and $R^4$ are joined together to form a saturated ring of 4,5 or 6 carbon atoms (spiro cycloalkyl)

or $R^1$ and $R^2$ or $R^3$ and $R^4$ are joined together to form a five or six membered saturated heterocyclic ring containing 1 or 2 heteroatoms chosen from oxygen or sulfur;

$R^5$ is H, alkyl, alkoxy;

$R^6$ is alkyl, alkoxy;

$R^7$ is H, alkyl, $(R^{11})_{1-3}$-phenyl;

$R^8$ and $R^9$ is each independently H, hydroxy alkyl, or $COR^5$;

$R^{10}$ is alkoxy, $(R11)_{1-3}$-phenylalkyl, $(R^{11})_{1-3}$-pyridylalkyl, $(R^{11})_{1-3}$-phenylalkoxy or $(R^{11})_{1-3}$-pyridylalkoxy;

$R^{11}$ is H, halogen, alkyl, hydroxy, hydroxy alkyl, alkoxy, CF3, CN, $COR^5$, $S(O)_{0-2}Me$;

$R^{12}$ is $S(O)_{0-2}Me$, $SO_2NH_2$;

or a pharmaceutically acceptable salt thereof.

Another preferred embodiment of the present invention is that wherein $R^1$ and $R^2$ in formula Ia are joined together to form a double bonded oxygen (=O).

Another preferred embodiment of the present invention is that wherein $R^3$ and $R^4$ in formula Ia are joined together to form a double bonded oxygen (=O).

Another preferred embodiment of the present invention is that wherein $R^3$ and $R^4$ in formula Ia are joined together to form a double bonded carbon atom ($=CR^8R^9$).

Another preferred embodiment of the present invention is that wherein $R^3$ and $R^4$ in formula Ia are joined together to form a double bonded substituted nitrogen atom ($=NR^{10}$).

Another preferred embodiment of formula Ia is that wherein $R^{12}$ is $SO_2Me$ or $SO_2NH_2$.

The invention is illustrated by the compounds of Examples 1 through 71 as disclosed herein as well as the compounds of Tables 1 through 6.

The following abbreviations have the indicated meanings:

Ace-$d_6$=acetone-$d_6$
Ac=acetyl
AcOH=acetic acid
AA=arachidonic acid
AIBN=2,2-azobisisobutyronitrile
Ar=aryl
Bn=benzyl
DIBAL=diisobutyl aluminium hydride
DMAP=4-(dimethylamino)pyridine
DMF=N,N-dimethylformamide
DMSO=dimethyl sulfoxide
EDTA=ethylenediaminetetraacetic acid
$Et_3N$=triethylamine
HBSS=Hanks balanced salt solution
HEPES=N-[2-Hydroxyethyl]piperazine-$N^1$-[2-ethanesulfonic acid]
HWB=human whole blood
KHMDS=potassium hexamethyldisilazane
LAH=lithium aluminium hydride
LDA=lithium diisopropylamide
LPS=lipopolysaccharide
MMPP=monoperoxyphtalic acid magnesium salt
NBS=N-bromosuccinimide
NSAID=non-steroidal anti-inflammatory drug
PCC=pyridinium chlorochromate
PDC=pyridinium dichromate
Ph=phenyl
Pyr=pyridinyl
r.t.=room temperature
rac.=racemic
TFAA=trifluoroacetic anhydride
Th=2- or 3-thienyl
THF=tetrahydrofuran
TLC=thin layer chromatography
TMEDA=N,N,N,N-tetramethylethylenediamine
TMSCl=chloro trimethylsilane
TsOH=p-toluenesulfonic acid
$SO_2Me$=methyl sulfone
$SO_2NH_2$=sulfonamide Alkyl group abbreviations Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Dose Abbreviations bid=bis in die=twice daily
qid=quater in die=four times a day
tid=ter in die=three times a day Alkyl, alkenyl, and alkynyl mean linear, branched and cyclic structures and combinations thereof.

The term "alkyl" means alkyl groups of from 1 to 7 carbon atoms. Examples of alkyl groups include methyl, ethyl, propyl, isopropyl, butyl, s- and t-butyl, pentyl, hexyl, heptyl, cyclopropyl, cyclohexyl and the like.

The term "alkenyl"means alkenyl groups of 2 to 7 carbon atoms. Examples of alkenyl groups are allyl, 5-hexen-1-yl, 2-methylpropen-1-yl, cyclopenten-4-yl and the like.

The term "alkynyl" means alkynyl groups of 2 to 7 carbon atoms. Examples of alkynyl groups are ethynyl, 2-pentyn-1-yl, 3,3-dimethyl-1-butyn-1-yl, and the like.

The term "alkoxy" means alkoxy groups of from 1 to 7 carbon atoms of a straight, branched, or cyclic configuration. Examples of alkoxy groups include methoxy, ethoxy, propoxy, isopropoxy, cyclopropyloxy, cyclohexyloxy, and the like.

The term "alkylthio" means alkylthio groups of from 1 to 7 carbon atoms of a straight, branched or cyclic configuration. Examples of alkylthio groups include methylthio, propylthio, isopropylthio, cycloheptylthio, etc. By way of illustration, the propylthio group signifies —$SCH_2CH_2CH_3$.

The term $(R^{11})_{1-3}$-phenyl indicates a phenyl group substituted with one to three $R^{11}$ substituents; $(R^{11})_{1-3}$-pyridyl, $(R^{11})_{1-3}$-arylene and $(R^{11})_{1-3}$-naphthyl have similar meanings.

Some examples of arylene are furan, thiophene, N-methylpyrrole, oxazole, thiazole and N-methylimidazole.

Halogen includes F, Cl, Br, and I.

It is intended that the definitions of any substituent (e.g., $R^5$, $R^{10}$, $R^{11}$, $R^{12}$, etc.) in a particular molecule be independent of its definitions elsewhere in the molecule.

Optical Isomers—Diastereomers—Geometric Isomers

Some of the compounds described herein contain one or more asymmetric centres and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

Salts

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, N-(2-hydroxyethyl)piperidine, N-(2-hydroxyethyl)pyrrolidine, isopropylamine, lysine, methylglucamine, morpholine, piperazine, piperidine, polyamine resins, procaine, purines, theobromine, triethylamine, trimethylamine, tripropylamine, tromethamine, and the like.

Acid Salts

When the compound of the present invention is basic, salts may be prepared from pharmaceutically acceptable non-toxic acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment which follows, references to the compounds of Formula I are meant to also include the pharmaceutically acceptable salts.

Utilities

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumour growth and hence can be used in the treatment of cancer. Compound I may also be of use in the treatment and/or prevention of cyclooxygenase-mediated proliferative disorders such as may occur in diabetic retinopathy and tumour angiogenesis.

Compound I will also inhibit prostanoid-induced smooth muscle contraction by preventing the synthesis of contractile prostanoids and hence may be of use in the treatment of dysmenorrhea, premature labour, asthma and eosinophil related disorders. It will also be of use in the treatment of Alzheimer's disease and for decreasing bone loss particularly in postmenopausal women (i.e. treatment of osteoporosis).

By virtue of its high inhibitory activity against COX-2 and/or its specificity for COX-2 over COX-1, compound I will prove useful as an alternative to conventional NSAID'S, particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anaemia such as hypoprothrombinemia, haemophilia or other bleeding problems; kidney disease; those prior to surgery or taking anticoagulants.

Pharmaceutical Compositions

For the treatment of any of these cyclooxygenase mediated diseases compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating COX-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are examplified by those already mentioned above. Additional excipients, for example sweetening, flavouring and colouring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dose Ranges

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

Similarly, compound I, will be useful as a partial or complete substitute for conventional NSAID'S in preparations wherein they are presently co-administered with other agents or ingredients. Thus in further aspects, the invention encompasses pharmaceutical compositions for treating COX-2 mediated diseases as defined above comprising a non-toxic therapeutically effective amount of the compound of Formula I as defined above and one or more ingredients such as another pain reliever including acetaminophen or phenacetin; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levodesoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

Methods of Synthesis

Compounds of Formula I of the present invention may be prepared according to the synthetic routes outlines in schemes 1 to 7 and by following the methods described herein.

Scheme 1 Preparation of acetylenes

The bis(aryl)acetylenes V may be prepared in a multi-step sequence from 4-bromothioanisole. The 4-bromothioanisole or an appropriately substituted aryl halide is coupled with trimethylsilylacetylene or an appropiately substituted phenylacetylene with a catalysts such as bis (triphenylphosphine)palladium(II) dibromide and copper(I) iodide in an organic solvent such as toluene and a base such as triethylamine. The trimethylsilyl group can be removed using a base such as sodium methoxide in methanol. The thioether IV is oxidized to the sulfone V with an oxidizing agent such as oxone®, mCPBA or MMPP in solvents such as dichloromethane and/or methanol-water.

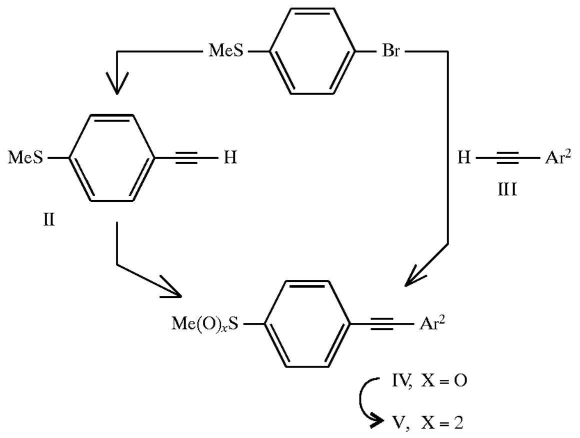

Scheme 2 Preparation of alkenes

The bis(aryl)ethylenes or stilbenes VII may be prepared from 4-bromothioanisole and an appropriately substituted styrene VI using a catalyst such as palladium(II) acetate, with salts such as LiCl, LiOAc and $nBU_4NCl$ and an organic solvent such as DMF. The stilbenes VII can also be prepared from an appropriately substituted $Ar^2$ halide and 4-methylthiostyrene. The latter is obtained from a Wittig type olefination between 4-methylthiobenzaldehyde and methyltriphenylphosphonium bromide with a base such as potassium t-butoxide in a solvent such as THF. Alternately, the stilbenes are prepared by a Wittig type olefination with 4-methylthiobenzaldehyde and an appropriately substituted benzylic phosphonium salts VIII in a solvent such as THF or in a two step sequence using a Grignard type condensation with appropriately substituted benzylic magnesium salts IX followed by elimination of the corresponding secondary alcohol with an acid such as TsOH in a solvent such as toluene.

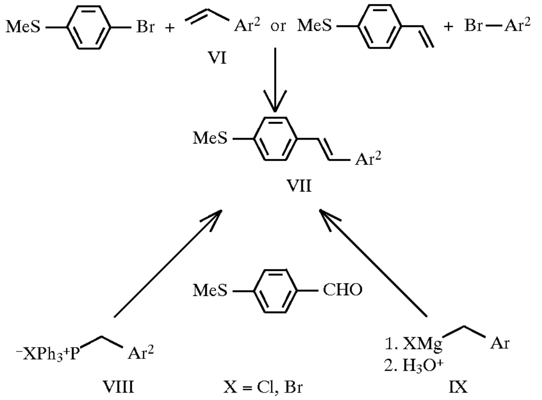

Scheme 3 Preparation of cyclobutenones

The cyclobutenones Ib and Ic may be prepared in a multi-step sequence, from stilbene VII of scheme 2. The cyclobutanones XI and XII(X=O) are obtained by a [2+2] cycloaddition between keteneiminium salts obtained from a N,N-dimethylamide X and a stilbene VII by a procedure analogous to the one described by L. Ghosez, et al., [*Org. Synth.,* 69, 199 (1990)]. The thioethers XI and XII (X=0) can be oxidized first to the sulfones (X=2) with an oxidizing agent such as oxone®, mCPBA or MMPP in solvents such as dichloromethane and/or methanol-water, and then the regioisomers are separated by flash chromatography before being further oxidized to the cyclobutenones Ib and Ic (X=2) using for example NBS in a solvant such as $CCl_4$. The sequence of oxidation can also be reversed; going from cyclobutanone XI (X=0) to cyclobutenone Ib (X=0), followed by oxidation to sulfone Ib (X=2). The sulfoxides (X=1) can be prepared by limiting the amount of the oxidizing agent.

by a procedure analogous to the one described by L. Ghosez, et al., [*Tetrahedron Lett.,* 25, 5043 (1984)]. Alternately, the cyclobutenones Ib and Ic (X=0) can be obtained by a [2+2] cycloaddition between keteneiminium salts obtained from trichloroacetylchloride X (Y=Cl) and Zn by a procedure analogous to the one described by A. Hassner, et al., [*Synthesis.,* 689 (1979)]. The derivatives obtained this way (Ib and Ic $R^1$,$R^2$=Cl) contains halides that can be reduced partially or totally to the alkenone (Ib and Ic $R^1$,$R^2$=H) using a metal such as zinc in solvents such as AcOH, ethanol and TMEDA, a procedure similar to the one described by R. L. Danheiser, et al., [*Tetrahedron Lett.,* 28, 3299 (1987)]. The thioether Ib and Ic (X=0) can be oxidized to the sulfoxides (X=1) or to the sulfones (X=2) with an oxidizing agent such as oxone®, mCPBA, MMPP in solvents such as dichloromethane and/or methanol-water. The two regioisomers are

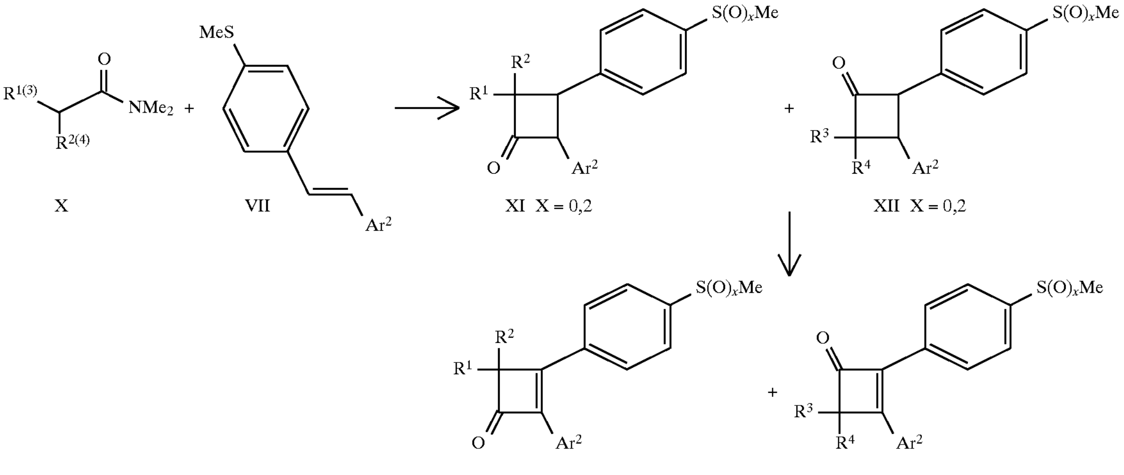

X VII XI X = 0,2 XII X = 0,2

Ib X = 0,1,2 Ic X = 0,1,2

Note: $R^1$,$R^2$ = $R^3$,$R^4$

Scheme 4 Preparation of cyclobutenones

The cyclobutenones Ib and Ic may be prepared in a multi-step sequence, from bis(aryl)acetylenes IV or V of Scheme 1. The cyclobutenones Ib and Ic can be obtained by a [2+2] cycloaddition between keteneiminium salts obtained from a N,N-dimethylamide X (Y=$NMe_2$) and acetylene V separated by flash chromatography. The sulfoxide Ib (X=1) can be further transformed into the sulfonamide Id in a 3 step sequence which involves sequencial treatment with an acid anhydride such as TFAA, followed by $Cl_{12}$ in AcOH and then ammonium hydroxide in organic solvents such as dichloromethane and THF.

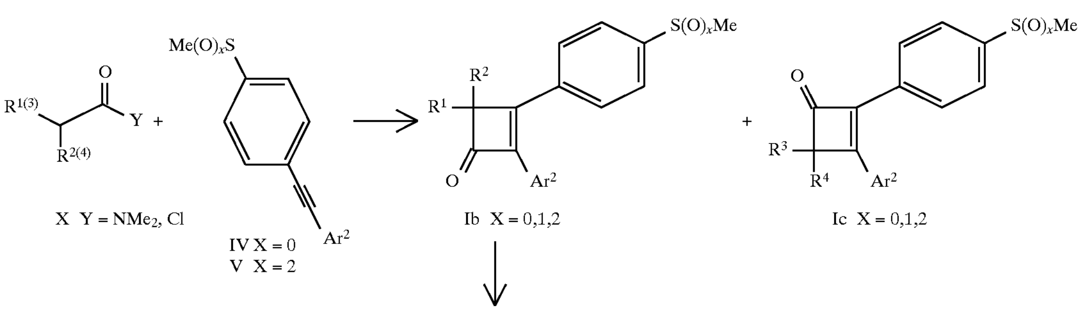

X Y = $NMe_2$, Cl

IV X = 0
V X = 2

Ib X = 0,1,2 Ic X = 0,1,2

-continued

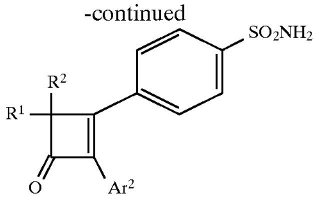

Id

Note: $R^1,R^2 = R^3,R^4$

Scheme 5 Preparation of cyclobutenes

The cyclobutenones Ib and Ic (X=2) may serves as precursors to various other derivatives as shown in Scheme 5. The cyclobutadienes Ig and Ih ($R^8,R^9$=H) can be obtained using an olefinating agent such as Tebbe's reagent or a Wittig type reagent such as methyltriphenylphosphonium bromide with a base such as potassium t-butoxide in an organic solvent such as THF. Likewise, the substituted analogs Ig and Ih ($R^8,R^9$=H, $CO_2Et$ and $R^8,R^9$=Me, $CO_2Et$) are prepared using a stabilised Wittig type reagent such as ethyl triphenylphosphoranylidene acetate or (carbethoxyethylidene)triphenylphosphorane in a solvent such as benzene. The ester function can be reduce to the corresponding alcohols Ig and Ih ($R^8,R^9$=H, $CH_2OH$ and $R^8,R^9$=Me, $CH_2OH$) according to standard organic procedures. Other derivatives such as imines and oximes Ie and If can be obtained by treating the cyclobutanones Ib and Ic with various hydroxylamine hydrochlorides in organic solvents such as pyridine and/or ethanol or with amines such as benzylamine using an acid such as TsOH in a solvent such as toluene. Some O-alkyloximes are obtained by alkylating oximes Ie and If ($R^{10}$=OH) using a base such as cesium carbonate and various alkylating agents such as 3-picolylchloride hydrochloride in a solvent such as DMF.

The carbonyl function of the cyclobutenones Ib and Ic may be reduced to the secondary alcohol and then alkylated or acylated using standard organic procedures to derivatives Ik and Im or transformed into an halide such as the fluoro analog Ij using diethylaminosulfur trifluoride in a solvent such as chloroform. The carbonyl function may be converted to a dithioacetal derivative Ii by treatment with an dithiol like 1,2-ethanedithiol, and acid such as boron trifluoride etherate in a solvent such as dichloromethane.

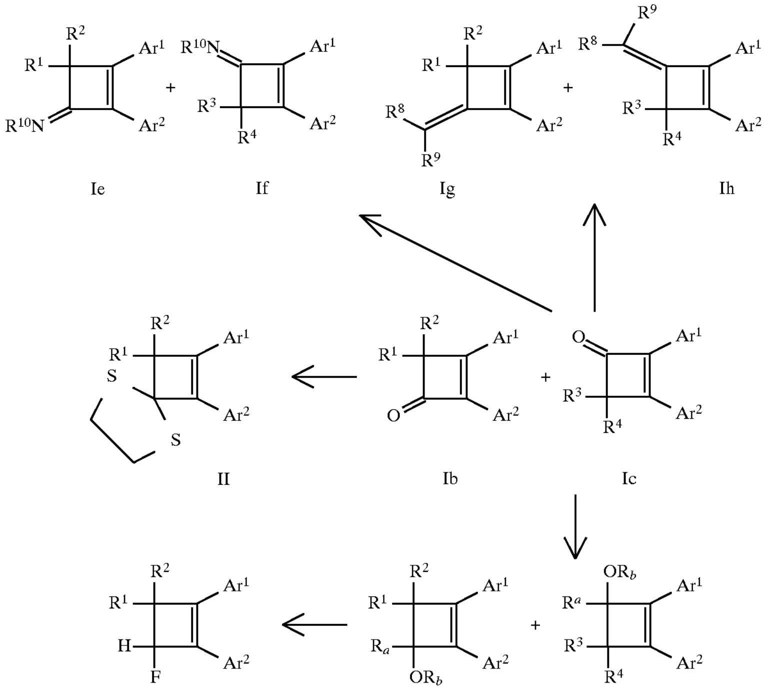

Ie If Ig Ih

II Ib Ic

Ij Ik Im $R_a$ = H, alkyl
$R_b$ = H, alkyl, $COR^5$

Scheme 6 Preparation of cyclobutenes

The cyclobutene In may be prepared in a multi-step sequence from 3-benzoylpropionic acid. The acid can be converted to the acid chloride using standard organic procedures and then used in a Friedel-Crafts type acylation of thioanisole with a Lewis acid such as aluminum chloride in a solvent such as dichloromethane to diketone XIV. The diketone XIV can be cyclised to the cyclobutene In (X=2) using metals such as titanium tetrachloride and zinc in a solvent such as THF. The sulfide is then oxidized to the sulfone In (X=2) as described in Scheme 1.

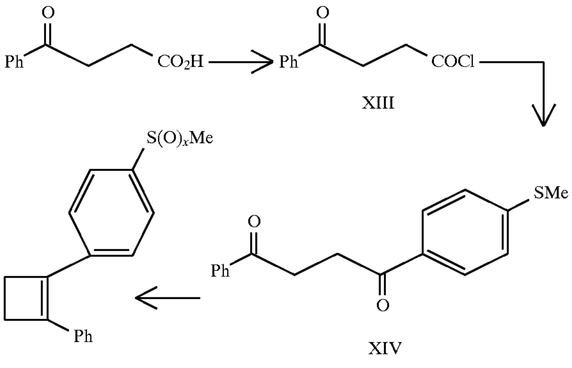

XIII

XIV

In X = 0,2

Scheme 7 Preparation of cyclobutenones

The cyclobutenes Io to Is may be prepared in a multi-step sequence from the dialkyl squarate XV. The key intermediate Io and the cyclobutene-1,2 dione Is can be obtained by a sequence similar to the one described by L. S. Liebeskind, et al., [*J. Org. Chem.,* 55, 5350 (1990)]. The analog Iq can be prepared from the reaction of intermediate Io with a stabilized Wittig type reagent such as methyl triphenylphosphoranylidene acetate in a solvent such as toluene. The cyclobutenone Ir can then be obtained after hydrolysis of the acetal using an acid such as sulfuric acid in solvents such as ethanol-water. The derivatives Ip may be derived from addition of nucleophiles such as RcLi to the ketone function of intermediate Io to produce the alcohols XX. Those can then be O-alkylated using standard organic procedures to XXI and the acetal hydrolysed as described earlier. By reversing the order in which $Ar^1Li$ and $Ar^2Li$ are reacted with XV, The opposite regioisomers to those depicteds in Io-s are obtained.

Representative Compounds

Table 1 illustrates compounds of formula I, which are representatives of the present invention.

TABLE 1

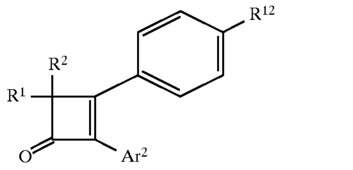

I b,d,o,p,r,s

| Ex. | $Ar^2$ | $R^1$ | $R^2$ | $R^{12}$ |
|---|---|---|---|---|
| 1 | Ph | Cl | Cl | SMe |
| 2 | Ph | Cl | Cl | $SO_2Me$ |
| 3 | Ph | H | Cl | $SO_2Me$ |
| 4 | Ph | H | H | SO2Me |
| 5 | 4F-$C_6H_4$ | Cl | Cl | $SO_2Me$ |
| 6 | Ph | Me | 3-Th | $SO_2Me$ |
| 7 | Ph | Me | 2-Th | $SO_2Me$ |
| 8 | Ph | Me | Ph | $SO_2Me$ |
| 9 | Ph | $-CH_2(CH_2)_3CH_2-$ | | $SO_2Me$ |
| 10 | Ph | $-CH_2(CH_2)_2CH_2-$ | | $SO_2Me$ |
| 11 | Ph | $-OCH_2CH_2O-$ | | $SO_2Me$ |
| 12 | Ph | =O | | $SO_2Me$ |
| 13 | Ph | Me | OMe | $SO_2Me$ |
| 14 | Ph | n-Bu | OMe | $SO_2Me$ |
| 15 | Ph | $=CHCO_2Me$ | | $SO_2Me$ |
| 16 | Ph | Me | Me | $SO_2Me$ |
| 17 | 3F-$C_6H_4$ | Me | Me | $SO_2Me$ |
| 18 | 4F-$C_6H_4$ | Me | Me | $SO_2Me$ |
| 19 | 3,5F-$C_6H_3$ | Me | Me | $SO_2Me$ |
| 20 | 3,4F-$C_6H_3$ | Me | Me | $SO_2Me$ |
| 21 | Ph | Me | Me | SMe |
| 22 | Ph | Me | Me | S(O)Me |
| 23 | Ph | Me | Me | $SO_2NH_2$ |

Table 2 illustrates compounds of formula I, which are further representatives of the present invention.

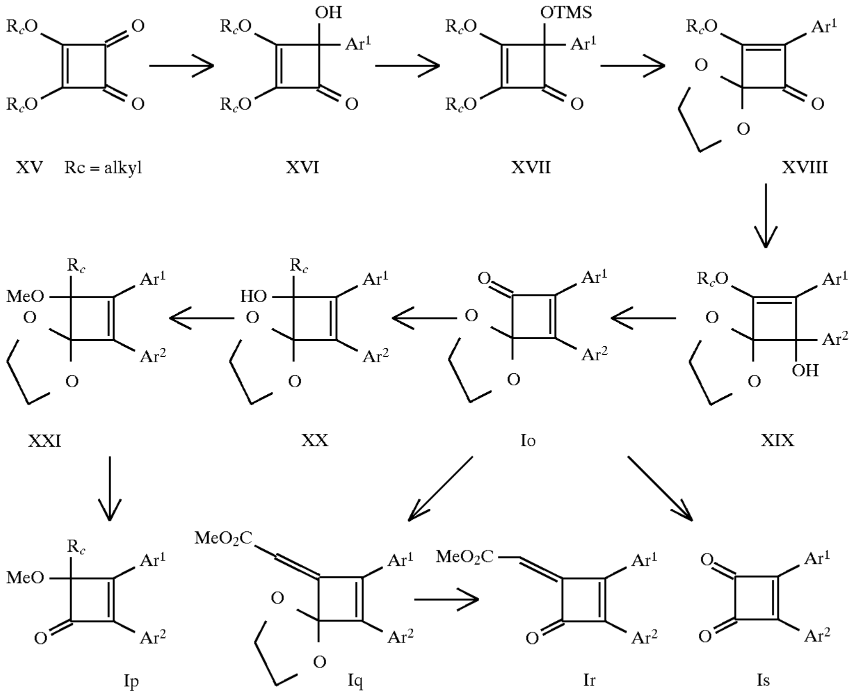

XV Rc = alkyl

XVI

XVII

XVIII

XXI

XX

Io

XIX

Ip

Iq

Ir

Is

TABLE 2

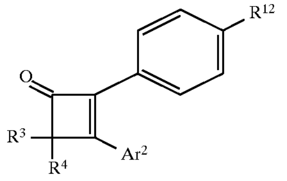

I c

| Ex. | $Ar^2$ | $R^3$ | $R^4$ | $R^{12}$ |
|---|---|---|---|---|
| 24 | Ph | Me | 3-Th | $SO_2Me$ |
| 25 | Ph | $-CH_2(CH_2)_3CH_2-$ | | $SO_2Me$ |
| 26 | Ph | $-CH_2(CH_2)_2CH_2-$ | | $SO_2Me$ |
| 27 | Ph | $-CH_2CH_2CH_2-$ | | $SO_2Me$ |
| 28 | $3F-C_6H_4$ | Me | Me | $SO_2Me$ |
| 29 | $4F-C_6H_4$ | Me | Me | $SO_2Me$ |
| 30 | Ph | Me | Me | $SO_2Me$ |
| 31 | Ph | Me | Me | SMe |
| 32 | Ph | Me | Me | SOMe |
| 33 | $4SO_2Me-C_6H_4$ | Me | Me | $SO_2Me$ |
| 34 | Ph | Me | H | $SO_2Me$ |
| 35 | Ph | H | i-Pr | $SO_2Me$ |

Table 3 illustrates compounds of formula I, which are further representatives of the present invention.

TABLE 3

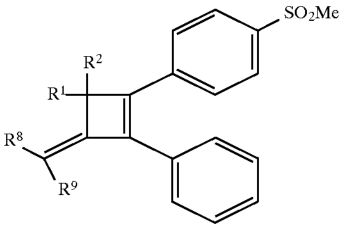

I g

| Ex. | $R^1$ | $R^2$ | $R^8$ | $R^9$ |
|---|---|---|---|---|
| 36 | Cl | Cl | H | H |
| 37 | Cl | Cl | H | $CO_2Et$ |
| 38 | Cl | Cl | H | $CH_2OH$ |
| 39 | H | H | H | H |
| 40 | H | H | $CO_2Et$ | H |
| 41 | H | H | H | $CO_2Et$ |
| 42 | H | H | Me | $CH_2OH$ |
| 43 | H | H | $CH_2OH$ | Me |
| 44 | Me | Me | H | H |

Table 4 illustrates compounds of formula I, which are further representatives of the present invention.

TABLE 4

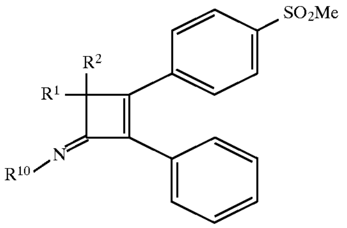

I e

| Ex. | $R^1$ | $R^2$ | $R^{10}$ |
|---|---|---|---|
| 45 | Me | Me | OH |
| 46 | Me | Me | O-t-Bu |
| 47 | Me | Me | OMe |
| 48 | Me | Me | $OCH_2Ph$ |

TABLE 4-continued

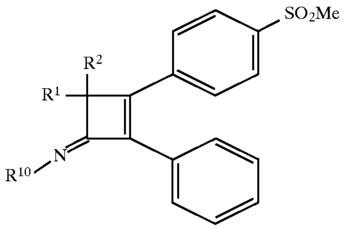

I e

| Ex. | $R^1$ | $R^2$ | $R^{10}$ |
|---|---|---|---|
| 49 | Me | Me | $CH_2Ph$ |
| 50 | Me | Me | $OCH_2$(3-Pyr) |
| 51 | Me | Me | $OCH_2$(2-Pyr) |
| 52 | Me | Me | $OCH_2(3-CO_2Me-Ph)$ |
| 53 | Me | Me | $OCH_2(3-CO_2H-Ph)$ |
| 54 | H | H | OH |
| 55 | H | H | O-t-Bu |
| 56 | H | H | OMe |
| 57 | H | H | $OCH_2Ph$ |

Table 5 illustrates compounds of formula I, which are further representatives of the present invention.

TABLE 5

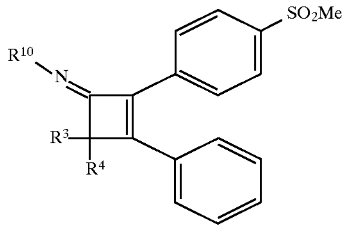

If

| Ex. | $R^3$ | $R^4$ | $R^{10}$ |
|---|---|---|---|
| 58a | Me | Me | O-t-Bu |
| 58b | Me | Me | O-t-Bu |
| 59 | Me | Me | $OCH_2Ph$ |

Table 6 illustrates compounds of formula I, which are further representatives of the present invention.

TABLE 6

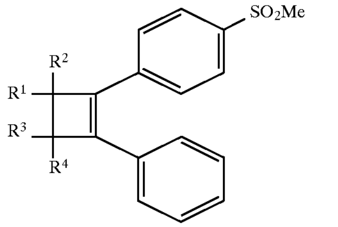

I i,j,k,m

| Ex. | $R^1$ | $R^2$ | $R^3$ | $R^4$ |
|---|---|---|---|---|
| 60 | H | H | H | H |
| 61 | Me | Me | Me | OH |
| 62 | Me | Me | H | OH |
| 63 | Me | Me | H | OMe |
| 64 | Me | Me | H | OAc |
| 65 | Me | Me | H | OCO-t-Bu |
| 66 | Me | Me | H | F |
| 67 | Me | Me | H | OCONHPh |
| 68 | Me | Me | $-SCH_2CH_2S-$ | |
| 69 | H | OH | Me | Me |
| 70 | H | OMe | Me | Me |

TABLE 6-continued

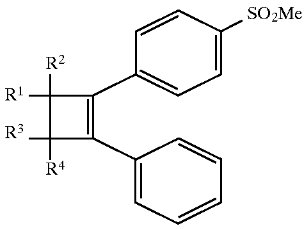

I i,j,k,m

| Ex. | $R^1$ | $R^2$ | $R^3$ | $R^4$ |
|---|---|---|---|---|
| 71 | H | OAc | Me | Me |

Assays for Determining Biological Activity

The compound of Formula I can be tested using the following assays to determine their COX-2 inhibiting activity.

INHIBITION OF CYCLOOXYGENASE ACTIVITY

Compounds are tested as inhibitors of cyclooxygenase activity in whole cell cyclooxygenase assays. Both of these assays measure prostaglandin $E_2$ synthesis in response to arachidonic acid, using a radioimmunoassay. Cells used for these assays are human osteosarcoma 143 cells (which specifically express COX-2) and human U-937 cells (which specifically express COX-1). In these assays, 100% activity is defined as the difference between prostaglandin $E_2$ synthesis in the absence and presence of arachidonate.

Whole Cell Assays

For cyclooxygenase assays, osteosarcoma cells are cultured in 1 mL of media in 24-well multidishes (Nunclon) until confluent ($1–2\times10^5$ cells/well). U-937 cells are grown in spinner flasks and resuspended to a final density of $1.5\times10^6$ cells/mL in 24-well multidishes (Nunclon). Following washing and resuspension of osteosarcoma and U-937 cells in 1 mL of HBSS, 1 $\mu$L of a DMSO solution of test compound or DMSO vehicle is added, and samples gently mixed. All assays are performed in triplicate. Samples are then incubated for 5 or 15 minutes at 37° C., prior to the addition of arachidonic acid. Arachidonic acid (peroxide-free, Cayman Chemical) is prepared as a 10 mM stock solution in ethanol and further diluted 10-fold in HBSS. An aliquot of 10 $\mu$L of this diluted solution is added to the cells to give a final arachidonic acid concentration of 10 $\mu$M. Control samples are incubated with ethanol vehicle instead of arachidonic acid. Samples are again gently mixed and incubated for a further 10 min. at 37° C. For osteosarcoma cells, reactions are then stopped by the addition of 100 $\mu$L of 1N HCl, with mixing and by the rapid removal of the solution from cell monolayers. For U-937 cells, reactions are stopped by the addition of 100 $\mu$L of 1N HCl, with mixing. Samples are then neutralized by the addition of 100 $\mu$L of 1N NaOH and $PGE_2$ levels measured by radioimmunoassay.

Whole cell assays for COX-2 and COX-1 using CHO transfected cell lines

Chinese hamster ovary (CHO) cell lines which have been stably transfected with an eukaryotic expression vector pCDNAIII containing either the human COX-1 or COX-2 cDNA's are used for the assay. These cell lines are referred to as CHO [hCOX-1] and CHO [hCOX-2], respectively. For cyclooxygenase assays, CHO[hCOX-1] cells from suspension cultures and CHO[hCOX-2] cells prepared by trypsinization of adherent cultures are harvested by centrifugation (300×g, 10 min) and washed once in HBSS containing 15 mM HEPES, pH 7.4, and resuspended in HBSS, 15 mM HEPES, pH 7.4, at a cell concentration of $1.5\times10^6$ cells/ml. Drugs to be tested are dissolved in DMSO to 66.7-fold fold the highest test drug concentration. Compounds are typically tested at 8 concentrations in duplicate using serial 3-fold serial dilutions in DMSO of the highest drug concentration. Cells ($0.3\times10^6$ cells in 200 $\mu$l) are preincunbated with 3 $\mu$l of the test drug or DMSO vehicle for 15 min at 37° C. Working solutions of peroxide-free AA (5.5 $\mu$M and 110 $\mu$M AA for the CHO [hCOX-1] and CHO [COX-2] assays, respectively) are prepared by a 10-fold dilution of a concentrated AA solution in ethanol into HBSS containing 15 mM HEPES, pH 7.4. Cells are then challenged in the presence or absence of drug with the AA/HBSS solution to yield a final concentration of 0.5 $\mu$M AA in the CHO[hCOX-1] assay and a final concentration of 10 $\mu$M AA in the CHO[hCOX-2] assay. The reaction is terminated by the addition of 10 $\mu$l 1N HCl followed by neutralization with 20 $\mu$l of 0.5N NaOH. The samples are centrifuged at 300×g at 4° C. for 10 min, and an aliquot of the clarified supernatant is appropriately diluted for the determination of $PGE_2$ levels using an enzyme-linked immunoassay for $PGE_2$ (Correlate $PGE_2$ enzyme immunoassay kit, Assay Designs, Inc.). Cyclooxygenase activity in the absence of test compounds is determined as the difference in $PGE_2$ levels of cells challenged with arachidonic acid versus the $PGE_2$ levels in cells mock-challenged with ethanol vehicle. Inhibition of $PGE_2$ synthesis by test compounds is calculated as a percentage of the activity in the presence of drug versus the activity in the positive control samples.

Assay of COX-1 Activity from U937 cell microsomes

U937 cells are pelleted by centrifugation at 500×g for 5 min and washed once with phosphate-buffered saline and repelleted. Cells are resuspended in homogenization buffer consisting of 0.1M Tris-HCl, pH 7.4, 10 mM EDTA, 2 $\mu$g/ml leupeptin, 2 $\mu$g/ml soybean trypsin inhibitor, 2 $\mu$g/ml aprotinin and 1 mM phenyl methyl sulfonyl fluoride. The cell suspension is sonicated 4 times for 10 sec and is centrifuged at 10,000×g for 10 min at 4° C. The supernatant is centrifuged at 100,000×g for 1 hr at 4° C. The 100,000×g microsomal pellet is resuspended in 0.1M Tris-HCl, pH 7.4, 10 mM EDTA to approximately 7 mg protein/ml and stored at −80° C.

Microsomal preparations are thawed immediately prior to use, subjected to a brief sonication, and then diluted to a protein concentration of 125 $\mu$g/ml in 0.1M Tris-HCl buffer, pH 7.4 containing 10 mM EDTA, 0.5 mM phenol, 1 mM reduced glutathione and 1 $\mu$M hematin. Assays are performed in duplicate in a final volume of 250 $\mu$l. Initially, 5 $\mu$l of DMSO vehicle or drug in DMSO are added to 20 $\mu$l of 0.1M Tris-HCl buffer, pH 7.4 containing 10 mM EDTA in wells of a 96-deepwell polypropylene titre plate. 200 $\mu$l of the microsomal preparation are then added and pre-incubated for 15 min at room temperature before addition of 25 $\mu$l of 1M arachidonic acid in 0.1M Tris-HCl and 10 mM EDTA, pH 7.4. Samples are incubated for 40 min at room temperature and the reaction is stopped by the addition of 25 $\mu$l of 1N HCl. Samples are neutralized with 25 $\mu$l of 1N NaOH prior to quantitation of $PGE_2$ content by radioimmunoassay (Dupont-NEN or Amersham assay kits). Cyclooxygenase activity is defined as the difference between $PGE_2$ levels in samples incubated in the presence of arachidonic acid and ethanol vehicle.

Assay of the activity of purified human COX-2

The enzyme activity is measured using a chromogenic assay based on the oxidation of N,N,N',N'-tetramethyl-p-phenylenediamine (TMPD) during the reduction of $PGG_2$ to $PGH_2$ by COX-2 (Copeland et al. (1994) Proc. Natl. Acad. Sci. 91, 11202–11206).

Recombinant human COX-2 is purified from Sf9 cells as previously described (Percival et al (1994) Arch. Biochem. Biophys. 15, 111–118). The assay mixture (180 μL) contains 100 mM sodium phosphate, pH 6.5, 2 mM genapol X-100, 1 μM hematin, 1 mg/ml gelatin, 80–100 units of purified enzyme (One unit of enzyme is defined as the amount of enzyme required to produce an O.D. change of 0.001/min at 610 nm) and 4 μL of the test compound in DMSO. The mixture is pre-incubated at room temperature (22° C.) for 15 minutes prior to initiation of the enzymatic reaction by the addition of 20 μL of a sonicated solution of 1 mM arachidonic acid (AA) and 1 mM TMPD in assay buffer (without enzyme or hematin). The enzymatic activity is measured by estimation of the initial velocity of TMPD oxidation over the first 36 sec of the reaction. A non-specific rate of oxidation is observed in the absence of enzyme (0.007–0.010 O.D. /min) and is subtracted before the calculation of the % inhibition. $IC_{50}$ values are derived from 4-parameter least squares non-linear regression analysis of the log-dose vs % inhibition plot.

HUMAN WHOLE BLOOD ASSAY

Rationale

Human whole blood provides a protein and cell-rich milieu appropriate for the study of biochemical efficacy of anti-inflammatory compounds such as selective COX-2 inhibitors. Studies have shown that normal human blood does not contain the COX-2 enzyme. This is consistent with the observation that COX-2 inhibitors have no effect on $PGE_2$ production in normal blood. These inhibitors are active only after incubation of human whole blood with LPS, which induces COX-2. This assay can be used to evaluate the inhibitory effect of selective COX-2 inhibitors on $PGE_2$ production. As well, platelets in whole blood contain a large amount of the COX-1 enzyme. Immediately following blood clotting, platelets are activated through a thrombin-mediated mechanism. This reaction results in the production of thromboxane $B_2$ ($TxB_2$) via activation of COX-1. Thus, the effect of test compounds on $TxB_2$ levels following blood clotting can be examined and used as an index for COX-1 activity. Therefore, the degree of selectivity by the test compound can be determined by measuring the levels of $PGE_2$ after LPS induction (COX-2) and $TxB_2$ following blood clotting (COX-1) in the same assay.

Method

A. COX-2 (LPS-induced $PGE_2$ production)

Fresh blood is collected in heparinized tubes by venipuncture from both male and female volunteers. The subjects have no apparent inflammatory conditions and have not taken any NSAIDs for at least 7 days prior to blood collection. Plasma is immediately obtained from a 2mL blood aliquot to use as blank (basal levels of $PGE_2$). The remaining blood is incubated with LPS (100 μg/ml final concentration, Sigma Chem, #L-2630 from *E. coli*; diluted in 0.1% BSA (Phosphate buffered saline) for 5 minutes at room temperature. Five hundred μL aliquots of blood are incubated with either 2 μL of vehicle (DMSO) or 2 μL of a test compound at final concentrations varying from 10 nM to 30 μM for 24 hours at 37° C. At the end of the incubation, the blood is centrifuged at 12,000×g for 5 minutes to obtain plasma. A 100 μL aliquot of plasma is mixed with 400μL of methanol for protein precipitation. The supernatant is obtained and is assayed for $PGE_2$ using a radioimmunoassay kit (Amersham, RPA#530) after conversion of $PGE_2$ to its methyl oximate derivative according to the manufacturer's procedure.

B. COX- 1 (Clotting-induced $TxB_2$ production)

Fresh blood is collected into vacutainers containing no anticoagulants. Aliquots of 500 μL are immediately transferred to siliconized microcentrifuge tubes preloaded with 2 μL of either DMSO or a test compound at final concentrations varying from 10 nM to 30 μM. The tubes are vortexed and incubated at 37° C. for 1 hour to allow blood to clot. At the end of incubation, serum is obtained by centrifugation (12,000×g for 5 min.). A 100 μL aliquot of serum is mixed with 400 μL of methanol for protein precipitation. The supernatant is obtained and is assayed for $TxB_2$ using a enzyme immunoassay kit (Cayman, #519031) according to the manufacturer's instruction.

RAT PAW EDEMA ASSAY

Protocol

Male Sprague-Dawley rats (150–200 g) are fasted overnight and are given, po, either vehicle (1% methocel or 5% Tween 80) or a test compound. One hr later, a line is drawn using a permanent marker at the level above the ankle in one hind paw to define the area of the paw to be monitored. The paw volume ($V_0$) is measured using a plethysmometer (Ugo-Basile, Italy) based on the principle of water displacement. The animals are then injected subplantarly with 50 ml of 1% carrageenan solution in saline (FMC Corp, Maine) into the paw using an insulin syringe with a 25-gauge needle (i.e. 500 mg carrageenan per paw). Three hr later, the paw volume ($V_3$) is measured and the increases in paw volume ($V_3$–$V_0$) are calculated. The animals are sacrificed by $CO_2$ asphyxiation and the absence or presence of stomach lesions scored. Data is compared with the vehicle-control values and percent inhibition calculated. All treatment groups are coded to eliminate observer bias.

NSAID-INDUCED GASTROPATHY IN RATS

Rationale

The major side effect of conventional NSAIDs is their ability to produce gastric lesions in man. This action is believed to be caused by inhibition of Cox-1 in the gastrointestinal tract. Rats are particularly sensitive to the actions of NSAIDs. In fact, rat models have been used commonly in the past to evaluate the gastrointestinal side effects of current conventional NSAIDs. In the present assay, NSAID-induced gastrointestinal damage is observed by measuring fecal $^{51}Cr$ excretion after systemic injection of $^{51}Cr$-labeled red blood cells. Fecal $^{51}Cr$ excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}Cr$-labeled red blood cells from a donor rat. The animals are placed individually in metabolism cages with food and water ad lib. Feces are collected for a 48 h period and $^{5}Cr$ fecal excretion is calculated as a percent of total injected dose. $^{51}Cr$-labeled red blood cells are prepared using the following procedures. Ten mL of blood is collected in heparinized tubes via the vena cava from a donor rat. Plasma is removed by centrifugation and replenished with equal volume of HBSS. The red blood cells are incubated with 400 Ci of sodium $^{51}$chromate for 30 min. at 37° C. At the end of the incubation, the red blood cells are washed twice with 20 mL HBSS to remove free sodium $^{51}$chromate. The red blood cells are finally reconstituted in 10 mL HBSS and 0.5 mL of the solution (about 20 Ci) is injected per rat.

PROTEIN-LOSING GASTROPATHY IN SQUIRREL MONKEYS

Rationale

Protein-losing gastropathy (manifested as appearance of circulating cells and plasma proteins in the GI tract) is a significant and dose-limiting adverse response to standard non-steroidal anti-inflammatory drugs (NSAIDs). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods Groups of male squirrel monkeys (0.8 to 1.4 kg) are treated by gavage with either 1% methocell or 5% Tween 80 in $H_2O$ vehicles, (3 mL/kg b.i.d.) or test compounds at doses from 1–100 mg/kg b.i.d. for 5 days. Intravenous $^{51}Cr$ (5 Ci/kg in 1 ml/kg phosphate buffer saline (PBS)) is administered 1 h after the last drug/vehicle dose, and feces collected for 24 h in a metabolism cage and assessed for excreted $^{51}Cr$ by gamma-counting. Venous blood is sampled 1 h and 8 h after the last drug dose, and plasma concentrations of drug measured by RP-HPLC.

Representative Biological Data

Compounds of the present invention are inhibitors of COX-2 and are thereby useful in the treatment of COX-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, COX-1 or COX-2 and a putative inhibitor. The $IC_{50}$ values represent the concentration of putative inhibitor required to lower $PGE_2$ synthesis to 50% of that obtained as compared to the uninhibited control.

The results for inhibition of $PGE_2$ production may be seen in Table 7.

TABLE 7

| Example | COX-2 $IC_{50}$ ($\mu$M) CHO cell lines | COX-1 $IC_{50}$ ($\mu$M) U-937 cells |
|---|---|---|
| 6 | 0.025 (n = 1) | 2.0 (n = 1) |
| 16 | 0.028 (n = 3) | 0.52 (n = 2) |
| 30 | 0.096 (n = 3) | 1.1 (n = 2) |
| 39 | 0.001 (n = 2) | 1.0 (n = 2) |
| 42 | 0.022 (n = 2) | 1.5 (n = 2) |

The invention will now be illustrated by the following nonlimiting examples in which, unless stated otherwise:

(i) all operations were carried out at room or ambient temperature, that is, at a temperature in the range 18°–25° C., (ii) evaporation of solvent was carried out using a rotary evaporator under reduced pressure (600–4000 pascals: 4.5–30 mmHg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; app. apparent; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliters), g (gram(s)), mg (milligrams(s)), mol (moles), mmol (millimoles), eq (equivalent(s)).

EXAMPLE 1

4,4-Dichloro-3-(4-methylthiophenyl)-2-phenyl-2-cyclobuten-1-one

To a suspension of l-(methylthio)-4-(phenylethynyl) benzene (method 6, 20 g) and Zn(Cu) couple (17.3 g) in anhydrous ether (450 mL) at 15° C. was added trichloroacetyl chloride (32.4 g) dropwise (over 3h). Internal temperature was maintained between 13°–16° C. during addition. The mixture was stirred at r.t. for 18 hr, filtered through a pad of celite®, washed with a saturated $NH_4Cl$ sol., saturated $NaCHO_3$ sol., brine, dried ($MgSO_4$) and the solvents evaporated. The resulting residue was first purified by flash chromatography (silica gel; hexane/EtOAc (98:2 to 90:10)) and then the resulting solid was stirred vigorously in $Et_2O$ for 3 hr and filtered to afford the title compound as a pale yellow solid, m.p. 99°–100° C.

EXAMPLE 2

4,4-Dichloro-3-(4-methylsulfonylphenyl)-2-phenyl-2-cyclobuten-1-one

To a solution of Example 1 (790mg) in $CH_2Cl_2$ (10 mL) and MeOH (10 mL) was added a solution of Oxone® (3.6 g) in $H_2O$ (10 mL). The mixture was stirred at r.t. for 2 hr and diluted with $Et_2O$. The organic phase was washed with $H_2O$, brine, dried ($MgSO_4$) and the solvents evaporated. The resulting solid residue was stirred vigorously in hexane/$Et_2O$ for 1 hr and then filtered to afford the title compound as a yellow solid, m.p. 124°–125° C.

EXAMPLES 3 AND 4

4-Chloro-3-(4-methylsulfonylphenyl)-2-phenyl-2-cyclobuten-1-one (Example 3) and 3-(4-methylsulfonylphenyl)-2-phenyl-2-cyclobuten-1-one (Example 4)

Step 1: 4-Chloro-3-(4-methylthiophenyl)-2-phenyl-2-cyclobuten-1-one and 3-(4-methylthiophenyl)-2-phenyl-2-cyclobuten-1-one To a solution of Example 1 (1.1 g) in EtOH (8 mL), AcOH (0.94 mL) and TMEDA (2.48 mL) at −20° C. was added Zinc powder (428 mg). The mixture was stirred at −20° C. for 1.5 hr, 0° C. for 2.5 hr, diluted with EtOAc, washed with HCl 1N, $H_2O$, a saturated $NaCHO_3$ sol., brine, dried ($MgSO_4$) and the solvents evaporated. The resulting residue was purified by flash chromatography (silica gel; hexane/EtOAc (90: 10 to 80:20)) to afford the title compounds as oils (less polar product; 4-Chloro-3-(4-methylthiophenyl)-2-phenyl-2-cyclobuten-1-one (example 3); $^1$H NMR (300 MHz, $CDCl_3$): δ 2.5 (s, 3H), 4.9 (s, 1H), 7.2–7.35 (m, 7H), 7.68 (d, 2H) and the more polar one; 3-(4-methylthiophenyl) -2-phenyl-2-cyclobuten-1-one (example 4); $^1$H NMR (300 MHz, $CDCl_3$): δ 2.58 (s, 3H), 3.6 (s, 2H), 7.35–7.50 (m, 5H), 7.68 (dd, 2H), 7.73 (d, 2H)).

Step 2: 4-Chloro-3-(4-methylsulfonylphenyl)-2-phenyl-2-cyclobuten-1-one (Example 3)

Following the procedure describe in Example 2, but substituting 4-chloro-3-(4-methylthiophenyl)-2-phenyl-2-cyclobuten-1-one from Step 1 for Example 1, the resulting residue was purified by flash chromatography (silica gel; hexane/EtOAc (80:20)) to afford the title compound as a yellow foam.

$^1$H NMR (300 MHz, $CDCl_3$): δ 3.04 (s, 3H), 5.02 (s, 1H), 7.2–7.35 (m, 5H), 7.9 (app.q, 4H).

3-(4-Methylsulfonylphenyl)-2-phenyl-2-cyclobuten-1-one (Example 4)

Following the procedure describe in Example 2, but substituting 3-(4-methylthiophenyl)-2-phenyl-2-cyclobuten-1-one from Step 1 for Example 1, the title compound was obtained as a yellow solid, m.p. 139°–140° C.

EXAMPLE 5

4,4-Dichloro-3-(4-methylsulfonylphenyl)-2-(4-fluorophenyl)-2-cyclobuten-1-one Step 1: 4,4-Dichloro-3-(4-methylthiophenyl)-2-(4-fluorophenyl)-2-cyclobuten-1-one Following the procedure describe in Example 1, but substituting 1-(methylthio)-4-(4-fluorophenylethynyl) benzene (method 6) for 1-(methylthio)-4-(phenylethynyl) benzene, the title compound was obtained as a yellow solid.

Step 2: 4,4-Dichloro-3-(4-methylsulfonylphenyl)-2-(4-fluorophenyl)-2-cyclobuten-1-one Following the procedure describe in Example 2, but substituting 4,4-Dichloro-3-(4-methylthiophenyl)-2-(4-fluorophenyl)-2-cyclobuten-1-one from Step 1 for Example 1, the title compound was obtained as a white solid, m.p. 116.5°–117.5° C.

EXAMPLES 6 AND 24

4-Methyl-3-(4-methylsulfonylphenyl)-2-phenyl-4-(3-thienyl)-2-cyclobuten-1-one (example 6) and 4-methyl-2-(4-methylsulfonylphenyl)-3-phenyl-4-(3-thienyl)-2-cyclobuten-1-one (example 24)

Step 1: N,N-Dimethyl-2-(3-thienyl)acetamide

To a solution of 3-thienyl acetic acid (5 g) in $CH_2Cl_2$ (40 mL) at r.t. was added oxalyl chloride (3.5 mL) dropwise and one drop of DMF. After 2 hr at r.t., the solvents were evaporated and the resulting acid chloride was diluted in THF (50 mL). Dimethyl amine was bubbled through the solution until the pH remained basic then NaOH 1N and $Et_2O$ were added. The organic phase was washed with $H_2O$, brine, dried ($MgSO_4$) and the solvents evaporated to afford the title product as an oil.

Step 2: N,N-Dimethyl-2-(3-thienyl)propionamide

To a solution of acetamide from Step 1 (510 mg) in THF (15 mL) at −78° C. was added LDA (mono THF, 1.5M, cyclohexane, 250 μL) followed by MeI (700 μL) after 30 min. The mixture was warmed to r.t., quenched with a saturated $NH_4Cl$ sol. and then extracted with $Et_2O$. The organic phase was washed with $H_2O$, brine, dried ($MgSO_4$) and the solvents evaporated. The residue was purified by flash chromatography (silica gel; hexane/EtOAc (60:40)) to afford the title compound as a oil.

Step 3: 4-Methyl-3-(4-methylsulfonylphenyl)-2-phenyl-4-(3-thienyl)-2-cyclobuten-1-one (Example 6) and 4-Methyl-2-(4-methylsulfonylphenyl)-3-phenyl-4-(3-thienyl)-2-cyclobuten-1-one (Example 24)

To a solution of acetamide from Step 2 (175 mg) in 1,2-dichloroethane (10 mL) at −20° C. was added triflic anhydride (175 μL) followed by 2,4,6-collidine (150 μL) and 1-(methylsulfonyl)-4-(phenylethynyl)benzene (method 7) (180 mg). The mixture was heated to reflux for 6 hr, cooled to r.t. and then diluted with NaOH 0.5N and ether. The organic phase was washed with $H_2O$, HCl 10%, $H_2O$, brine, dried ($MgSO_4$) and the solvents evaporated. The residue was purified by flash chromatography (silica gel; toluene/ether (95:5)) to afford the title compounds as a pale yellow solid for the more polar product (Example 6); m.p. 124°–125° C. and as a pale yellow foam for the less polar product (Example 24); $^1$H NMR (300 MHz, $CDCl_3$): δ 1.88 (s, 3H), 3.05 (s, 3H), 7.06 (q, 1H), 7.21 (q, 1H), 7.31 (q, 1H), 7.41 (m, 3H), 7.74 (m, 4H), 7.91 (m, 2H).

EXAMPLE 7

4-Methyl-3-(4-methylsulfonylphenyl)-2-phenyl-4-(2-thienyl)-2-cyclobuten-1-one Following the procedure describe in Example 6, but substituting 2-thienyl acetic acid for 3-thienyl acetic acid, the title product was obtained as a pale yellow foam (less polar product); $^1$H NMR (300 MHz, $CDCl_3$): δ 1.94 (s, 3H), 3.06 (s, 3H), 7.01 (m, 2H), 7.26 (m, 2H), 7.43 (m, 2H), 7.72 (m, 2H), 7.77 (d, 2H), 7.91 (d, 2H).

EXAMPLE 8

4-Methyl-3-(4-methylsulfonylphenyl)-2,4-diphenyl-2-cyclobuten-1-one

Following the procedure describe in Example 6, but substituting 2-phenyl propionic acid for 3-thienyl acetic acid and omitting step 2, the title product was obtained as a pale yellow foam (less polar product); $^1$H NMR (300 MHz, $CDCl_3$): δ 1.91 (s, 3H), 3.06 (s, 3H), 7.28–7.45 (m, 8H), 7.89 (m, 4H), 7.91 (d, 2H).

EXAMPLES 9 AND 25

3-(4-Methylsulfonylphenyl)-2-phenylspiro[4.6]-2-nonen-1-one (Example 9) and 2-(4-methylsulfonylphenyl)-3-phenylspiro[4.6]-2-nonen-1-one (Example 25)

Following the procedure describe in Example 6, but substituting cyclohexanecarboxylic acid for 3-thienyl acetic acid and omitting step 2, the title products were obtained as a off-white solids; 3-(4-methylsulfonylphenyl)-2-phenyl-spiro[4.6]-2-nonen-1-one (Example 9), m.p. 169° C. and 2-(4-methylsulfonylphenyl)-3-phenyl-spiro[4.6]-2-nonen-1-one (Example 25), m.p. 145° C.

EXAMPLES 10 AND 26

3-(4-Methylsulfonylphenyl)-2-phenylspiro[4.5]-2-octen-1-one (Example 10) and 2-(4-methylsulfonylphenyl)-3-phenylspiro[4.5]-2-octen-1-one (Example 26)

Following the procedure describe in Example 6, but substituting cyclopentanecarboxylic acid for 3-thienyl acetic acid and omitting step 2, the title products were obtained: 3-(4-methylsulfonylphenyl)-2-phenyl-spiro[4.5]-2-octen-1-one (Example 10) as an oil, $^1H$ NMR (300 MHz, $CDCl_3$): δ 1.8 (m, 4H), 2.0 (m, 2H), 3.08 (s, 3H), 7.35 (m, 3H), 7.6 (d, 2H), 7.98 (d, 2H) and 2-(4-methylsulfonylphenyl)-3-phenylspiro[4.5]-2-octen-1-one (Example 26) as a white solid, m.p. 98° C.

EXAMPLE 11

3-(4-Methylsulfonylphenyl)-4-phenyl-3-cyclobuten-1,2-dione-2-(ethylene acetal) (Following the general procedure as described in *J. Org. Chem.,* 1990, 55, 5351)

Step 1: 2,3-Diisopropoxy-4-hydroxy-4-phenyl-2-cyclobuten-1-one

To a solution of diisopropylsquarate (5 g) in THF (50 mL) at −10° C. was added PhMgBr (3M, $Et_2O$, 9 mL). After 30 min., the mixture was quenched with saturated $NH_4Cl$ sol. and extracted with $Et_2O$. The organic phase was washed with $H_2O$, brine, dried ($MgSO_4$) and the solvents evaporated. Flash chromatography of the residue (silica gel; hexane/EtOAc (85:15)) provided the title compound as an oil.

Step 2: 2,3-Diisopropoxy-4-phenyl-4-trimethylsilyloxy-2-cyclobuten-1-one

To a solution of alcohol from Step 1 (4.1 g) in $Et_2O$ (40 mL) at r.t. was added $Et_3N$ (6.2 mL) and TMSCl (2.8 mL). The mixture was stirred at r.t. for 48 hr, quenched with $H_2O$ and extracted with $Et_2O$. The organic phase was washed with $H_2O$, brine, dried ($MgSO_4$) and the solvents evaporated. Flash chromatography of the residue (silica gel; hexane/EtOAc (100:0 to 98:2)) provided the title compound as an oil.

Step 3: 3-Isopropoxy-4 phenyl-3-cyclobuten-1,2-dione-2-(ethylene acetal)

To a solution of cyclobutenone from Step 2 (3.9 g) in THF (12 mL) at r.t. was added 1,2 bis(trimethylsilyloxy)ethane (2.9 mL) and trimethylsilyl triflate (10 μL). The mixture was stirred at r.t. for 6 hr, filtered through a plug of silica gel and the solvents evaporated. The resulting solid residue was stirred vigorously in hexane/$Et_2O$ for 1 hr and then filtered to afford the title compound as a yellow solid.

Step 4: 3-(4-Methylthiophenyl)-4-phenyl-3-cyclobuten-1,2-dione-2-(ethylene acetal)

To a solution of 4-bromothioanisole (450 mg) in THF (20 mL) at −78° C. was added n-BuLi (2M, Hexane, 1.3 mL) dropwise. After 10 min. the cyclobutenone from Step 3 (400 mg) was added in one portion at −78° C. The mixture was stirred 10 more min., quenched with $H_2O$ and extracted with $Et_2O$. The organic phase was washed with $H_2O$, brine, dried ($MgSO_4$) and the solvents evaporated. The crude residue was diluted with THF (10 mL) and HCl 2N (1 mL) and the mixture stirred at r.t. for 3 hr. The organic phase was washed with $H_2O$, brine, dried ($MgSO_4$) and the solvents evaporated. Flash chromatography of the residue (silica gel; hexane/EtOAc (80:20)) provided the title compound as a yellow solid.

Step 5: 3-(4-Methylsulfonylphenyl)-4-phenyl-3-cyclobutene 1,2-dione-2-(ethylene acetal)

To a solution of cyclobutenone from Step 4 (254 mg) in $CHCl_3$ (10 mL) at r.t. was added 3-chloroperoxybenzoic acid (80–85%, 400 mg). The mixture was stirred at r.t. for 20 min. and $Ca(OH)_2$ (500 mg) was added. After 20 min., the heterogeneous solution was filtered and the solvents evaporated. The resulting solid residue was stirred vigorously in hexane/$Et_2O$ for 1 hr and then filtered to afford the title compound as a yellow solid, m.p. 166°–167° C.

EXAMPLE 12

3-(4-Methylsulfonylphenyl)-4-phenyl-3-cyclobuten-1,2-dione

To a solution of Example 11 (175 mg) in THF (10 mL) was added conc. $H_2SO4$ (0.5 mL). The mixture was stirred at r.t. for 16 hr, heated to reflux for 4 hr and then cooled to r.t. The organic phase was diluted with $Et_2O$, washed with $H_2O$, brine, dried ($MgSO_4$) and the solvents evaporated. The resulting solid residue was stirred vigorously in hexane/$Et_2O$ for 1 hr and then filtered to afford the title compound as a yellow solid, m.p. 139°–140° C.

EXAMPLE 13

4-Methoxy-4-methyl-3-(4-methylsulfonylphenyl)-2-phenyl-2-cyclobuten-1-one

Step 1: 2,3-Diisopropoxy-4-hydroxy-4-(4-methylthiophenyl)-2-cyclobuten-1-one

To a solution of 4-bromothioanisole (32.5 g) in THF (400 mL) at −78° C. was added n-BuLi (1.6M, Hexane, 100 mL) dropwise. After 15 min., a solution of diisopropylsquarate (20 g) in THF (200 mL) at −78° C. was added. After 30 min., the mixture was quenched with saturated $NH_4Cl$ sol. and extracted with $Et_2O$. The organic phase was washed with $H_2O$, brine, dried ($MgSO_4$) and the solvents evaporated. Flash chromatography of the residue (silica gel; hexane/EtOAc (85:15)) provided the title compound as a yellow solid.

Step 2: 4-(4-Methylthiophenyl)-3-phenyl-3-cyclobuten-1,2-dione-2-(ethylene acetal)

Following the procedure as described in Example 11, step 2 and 3, but substituting 2,3-diisopropoxy-4-hydroxy-4-(4-methylthiophenyl-2-cyclobuten-1-one for 2,3-diisopropoxy-4-hydroxy-4-phenyl-2-cyclobuten-1-one.

Step 3: 4-Methoxy-4-methyl-3-(4-methylthiophenyl)-2-phenyl-2-cyclobuten-1-one (ethylene acetal)

To a solution of cyclobutenone from step 2 (132 mg) in THF (10 mL) at −78° C. was added MeLi (1.6M, ether) dropwise until the reaction was completed by TLC. The mixture was quenched with $H_2O$ and ether. The organic phase was washed with $H_2O$, brine, dried ($MgSO_4$) and the solvents evaporated. The crude tertiary alcohol was dissolved in DMF (5 mL) and excess NaH (80%, 100 mg) and MeI (0.5 mL) was added. The mixture was stirred at r.t. 60 min., quenched with $H_2O$ and ether. The organic phase was washed with $H_2O$, brine, dried ($MgSO_4$) and the solvents evaporated to give the title product as an oil.

Step 4: 4-Methoxy-4-methyl-3-(4-methylthiophenyl)-2-phenyl-2-cyclobuten-1-one

Following the procedure as describe in Example 12, but substituting acetal from step 3 for Example 11, the title product was used as such in the next step.

Step 5: 4-Methoxy-4-methyl-3-(4-methylsulfonylphenyl)-2-phenyl-2-cyclobuten-1-one Following the procedure describe in Example 2, but substituting sulfide from Step 4 for Example 1, the title product was obtained as a yellow solid, m.p. 145° C.

EXAMPLE 14

4-Methoxy-4-butyl-3-(4-methylsulfonylphenyl)-2-phenyl-2-cyclobuten-1-one

Following the procedure described in Example 13 but substituting BuLi for MeLi in step 3, the title product was obtained as a oil, $^1$H NMR (300 MHz, $CDCl_3$): δ 0.8 (t, 3H), 1.3 (m, 4H), 1.9 (m, 1H), 2.05 (m, 1H), 3.1 (s, 3H), 3.4 (s, 3H), 7.43 (m, 3H), 7.7 (dd, 2H), 8.0 (dd, 4H).

EXAMPLE 15

(Z)-Methyl[4-(4-methylsulfonylphenyl)-3-phenyl-3-cyclobuten-2-one-1-ylidene]acetate Step 1: (Z)-Methyl [4-(4-methylthiophenyl)-3-phenyl-3-cyclobuten-2-one-1-ylidene (ethylene acetal)]acetate A solution of 4-(4-methylthiophenyl)-3-phenyl-3-cyclobutene 1,2-dione-2-(ethylene acetal) from Example 13, step 2 (250 mg) and methyl triphenylphosphoranylidene acetate (400 mg) in toluene (20 mL) was refluxed 16 hr, cooled to r.t. and the solvents evaporated. Flash chromatography of the residue (silica gel; hexane/EtOAc (80:20)) provided the title compound as a solid, m.p. 178° C.

Step 2: (Z)-Methyl [4-(4-methylthiophenyl)-3-phenyl-3-cyclobuten-2-one-1-ylidene]acetate Following the procedure described in Example 12 but substituting acetal from step 1 for 3-(4-Methylsulfonylphenyl)-4-phenyl-3-cyclobutene 1,2-dione-2-(ethylene acetal), the title product was used as such in the next step.

Step 3: (Z)-Methyl[4-(4-methylsulfonylphenyl)-3-phenyl-3-cyclobuten-2-one-1-ylidene]acetate Following the procedure describe in Example 2, but substituting sulfide from Step 2 for Example 1, the title product was obtained as an oil, $^1$H NMR (300 MHz, $CDCl_3$): δ 3.12 (s,3H), 3.80 (s, 3H), 5.69 (s, 1H), 7.3–7.5 (m, 3H), 7.8–7.9 (m, 4H), 8.11 (d, 2H).

EXAMPLES 16 AND 30

4,4-Dimethyl-3-(4-methylsulfonylphenyl)-2-phenyl-2-cyclobuten-1-one (example 16) and 4,4-dimethyl-2-(4-methylsulfonylphenyl)-3-phenyl-2-cyclobuten-1-one (example 30)

Step 1: (trans)-2,2-Dimethyl-3-(4-methylthiophenyl)-4-phenyl-1-cyclobutanone and (trans)-2,2-dimethyl-4-(4-methylthiophenyl)-3-phenyl-1-cyclobutanone To a solution of N,N-dimethyl-2-methylpropionamide (30.5 g) in 1,2-dichloroethane (1.0 L) at 0° C. was added triflic anhydride (54 mL) dropwise followed by a solution of 2,4,6-collidine (42 mL) and (E)-1-(methylthio)-4-(2-phenylethenyl)benzene (method 1 or 2, 60 g) in 1,2-dichloroethane (450 mL). The mixture was stirred at r.t. for 30 min., heated at reflux for 6 hr, cooled to r.t., and the solvent evaporated. The residue was dissolved in $CCl_4$ (450 mL) and $H_2O$ (225 mL) and the mixture refluxed for 18 hr. The organic phase was separated, the aqueous phase extracted with $CH_2Cl_2$ (2×), the combined organic phase was dried ($MgSO_4$) and the solvents evaporated. The resulting residue was purified by flash chromatography (silica gel; toluene/hexane (75:25)) to provide the mixture of title products (≈3:1) as an oil.

Step 2: (trans)-2,2-Dimethyl-3-(4-methylsulfonylphenyl)-4-phenyl-1-cyclobutanone and (trans)-2,2-dimethyl-4-(4-methylsulfonylphenyl)-3-phenyl-1-cyclobutanone Following the procedure described in method 7, but substituting cyclobutanone from step 1 for 1-(methylthio)-4-(phenylethynyl)benzene, after purification by flash chromatography (silica gel; hexane/EtOAc (70:30)) the title products were obtained as white solids: the major more polar (trans)-2,2-dimethyl-3-(4-methylsulfonylphenyl)-4-phenyl-1-cyclobutanone; $^1$H NMR (300 MHz, $CDCl_3$): δ 1.0 (s, 3H), 1.42 (s, 3H), 3.13 (s, 3H), 3.81 (d, 1H), 5.3 (d, 1H), 7.2–7.4 (m, 5H), 7.72 (d, 2H), 7.95 (d, 2H), the less polar minor (trans)-2,2-dimethyl-4-(4-methylsulfonylphenyl)-3-phenyl-1-cyclobutanone; $^1$H NMR (300 MHz, $CDCl_3$): δ 0.99 (s, 3H) ), 1.4 (s, 3H), 3.08 (s, 3H), 3.78 (d, 1H), 5.39 (d, 1H), 7.3–7.6 (m, 5H), 7.6 (d, 2H), 7.91 (d, 2H).

Step 3: 4,4-Dimethyl-3-(4-methylsulfonylphenyl)-2-phenyl-2-cyclobuten-1-one (example 16) and 4,4-dimethyl-2-(4-methylsulfonylphenyl)-3-phenyl-2-cyclobuten-1-one (Example 30)

To a solution of cyclobutanone from step 2 (7.9 g) in $CCl_4$ was added NBS (5.1 g). The mixture was heated to reflux for 1.5 hr, cooled to r.t. and the solvent evaporated. The resulting residue was purified by flash chromatography (silica gel; hexane/EtOAc (70:30)) to provide the title compound as a yellow solid. Example 16; m.p. 136°–138° C. Example 30; m.p. 134.5°–135.5° C.

EXAMPLES 17 AND 28

4,4-Dimethyl-3-(4-methylsulfonylphenyl)-2-(3-fluorophenyl)-2-cyclobuten-1-one (example 17) and 4,4-dimethyl-2-(4-methylsulfonylphenyl)-3-(3-fluorophenyl)-2-cyclobuten-1-one (example 28)

Following the procedure described in Example 16, but substituting (E)-1-(methylthio)-4-[2-(3-fluorophenyl)ethenyl]benzene (method 4) for (E)-1-(methylthio)-4-(2-phenylethenyl)benzene, the title products were obtained as yellow solids. Example 17; m.p. 127.5°–129° C. Example 28; m.p. 116.5°–117.5° C.

EXAMPLES 18 AND 29

4,4-Dimethyl-3-(4-methylsulfonylphenyl)-2-(4-fluorophenyl)-2-cyclobuten-1-one (example 18) and 4,4-dimethyl-2-(4-methylsulfonylphenyl)-3-(4-fluorophenyl)-2-cyclobuten-1-one (example 29)

Following the procedure described in Example 16, but substituting (E)-1-(methylthio)-4-[2-(4-fluorophenyl)ethenyl]benzene (method 3) for (E)-1-(methylthio)-4-(2-phenylethenyl)benzene, the title products were obtained as white solids. Example 18; m.p. 59°–60° C. Example 29; m.p. 124°–126° C.

EXAMPLE 19

4,4-Dimethyl-3-(4-methylsulfonylphenyl)-2-(3,5-difluorophenyl)-2-cyclobuten-1-one Following the procedure described in Example 16, but (E)-1-(methylthio)-4-[2-(3,5-difluorophenyl)ethenyl]benzene (method 4) for (E)-1-(methylthio)-4-(2-phenylethenyl)benzene, the title product was obtained as yellow solid; m.p. 113°–114° C.

EXAMPLE 20

4,4-Dimethyl-3-(4-methylsulfonylphenyl)-2-(3,4-difluorophenyl)-2-cyclobuten-1-one Following the procedure described in Example 16, but substituting (E)-1-(methylthio)-4-[2-(3,4-difluorophenyl)

ethenyl]benzene (method 5) for (E)-1-(methylthio)-4-(2-phenylethenyl)benzene, the title product was obtained as pink solid; m.p. 117.5°–118.5° C.

EXAMPLES 21 AND 31

4,4-Dimethyl-3-(4-methylthiophenyl)-2-phenyl-2-cyclobuten-1-one (example 21) and 4,4-dimethyl-2-(4-methylthiophenyl)-3-phenyl-2-cyclobuten-1-one (example 31)

Following the procedure described in Example 16, step 1 and step 3, gave the title products after purification by flash chromatography (silica gel; hexane/EtOAc (95:5)): Example 21 as a yellow oil; $^{1}H$ NMR (300 MHz, $CDCl_3$): δ 1.49 (s, 6H), 2.58 (s, 3H), 7.3–7.5 (m, 5H), 7.66 (d, 2H), 7.7 (d, 2H) and Example 31 as a yellow solid, m.p. 109°–110° C.

EXAMPLE 22

4,4-Dimethyl-3-(4-methylsulfinylphenyl)-2-phenyl-2-cyclobuten-1-one

To a solution of Example 21 (72 mg) in $CH_2Cl_2$ (2 mL) at 0° C. was added m-chloroperbenzoic acid (80%, 55 mg). The mixture was stirred at 0° C. 10 min., at r.t. for 30 min. and then $Ca(OH)_2$ (36 mg) was added. After 1 hr, the heterogeneous mixture was filtered and the solvent evaporated The resulting residue was purified by flash chromatography (silica gel; hexane/EtOAc (40:60)) to give the title compound as an orange oil; $^{1}H$ NMR (300 MHz, $CDCl_3$): δ 1.52 (s, 6H), 2.78 (s, 3H), 7.4–7.5 (m, 3H), 7.66 (dd, 2H), 7.81 (d, 2H), 7.98 (d, 2H).

EXAMPLE 23

4,4-Dimethyl-3-(4-aminosulfonylphenyl)-2-phenyl-2-cyclobuten-1-one

Step 1: 4,4-Dimethyl-2-(4-thiophenyl)-3-phenyl-2-cyclobuten-1-one

To a solution of Example 22 (148 mg) in $CH_2Cl_2$ (2 mL) was added trifluoroacetic anhydride (240 μL). The mixture was stirred at reflux for 40 min., cooled to r.t., quenched with $MeOH/Et_3N$ (1:1) and the solvents evaporated to give the crude thiol which was used as such in the next step.

Step 2: 4,4-Dimethyl-3-(4-chlorosulfonylphenyl)-2-phenyl-2-cyclobuten-1-one

To a solution of crude thiol from step 1 in degassed $CH_2Cl_2$ (2 mL) at 0° C., was added a sol. of $Cl_2$ in AcOH (1M, 1.9 mL). After 60 min. the mixture was poured into ice and $CH_2Cl_2$. The organic phase was separated, washed with saturated $NaCHO_3$ sol., brine, dried ($MgSO_4$) and the solvents evaporated to give the crude sulfonyl chloride which was used as such in the next step.

Step 3: 4,4-Dimethyl-3-(4- aminosulfonylphenyl)-2-phenyl-2-cyclobuten-1-one

To a solution of crude sulfonyl chloride from step 2 (96 mg) in THF (2 mL) at 0° C. was added conc. $NH_4OH$ (77 μL). The mixture was stirred for 30 min., diluted with EtOAc, washed with $H_2O$, brine, dried ($MgSO_4$) and the solvents evaporated. Flash chromatography of the residue (silica gel; hexane/EtOAc (50:50)) gave the title compound as a yellow solid, m.p. 142.5°–144° C.

EXAMPLE 27

2-(4-Methylsulfonylphenyl)-3-phenylspiro[4.4]-2-hepten-1-one

Following the procedure describe in Example 6, but substituting cyclobutanecarboxylic acid for 3-thienyl acetic acid and omitting step 2, the title product was obtained as a pale yellow solid, m.p. 139° C.

EXAMPLE 32

4,4-Dimethyl-2-(4-methylsulfinylphenyl)-3-phenyl-2-cyclobuten-1-one

Following the procedure described in Example 22, but substituting Example 31 for Example 21, the resulting residue was purified by flash chromatography (silica gel; hexane/EtOAc (40:60)) to give the title compound as yellow solid, m.p. 104°–105° C.

EXAMPLE 33

4,4-Dimethyl-2,3-bis(4-methylsulfonylphenyl)-2-cyclobuten-1-one

Step 1: (trans)-2,2-Dimethyl-3,4-bis(4-methylthiophenyl)-1-cyclobutanone

To a solution of N,N-dimethyl-2-methylpropionamide (615 mg) in 1,2-dichloroethane (20 mL) at 0° C. was added triflic anhydride (1.51 g) dropwise followed by a solution of 2,4,6-collidine (715 mg) and (E)-1-(methylthio)-4-(2-phenylethenyl)benzene (730 mg, method 1) in 1,2-dichloroethane (5 mL). The mixture was stirred at r.t. for 30 min., heated at reflux for 6 hr, cooled to r.t., and the solvent evaporated. The residue was dissolved in $CCl_4$ (50 mL) and $H_2O$ (50 mL) and the mixture refluxed for 18 hr. The organic phase was separated, the aqueous phase extracted with $CH_2Cl_2$ (2×), the combined organic phase were dried ($MgSO_4$) and the solvents evaporated. The resulting residue was purified by flash chromatography (silica gel; toluene) to provide title product.

Step 2: (trans)-2,2-Dimethyl-3,4-bis(4-methylsulfonylphenyl)-1-cyclobutanone

Following the procedure describe in Example 2, but (trans)-2,2-dimethyl-3,4-bis(4-methylthiophenyl)-1-cyclobutanone from Step 1 for Example 1, the resulting residue was purified by flash chromatography (silica gel; hexane/EtOAc (80:20)) to afford the title compound.

Step 3: 4,4-Dimethyl-2,3-bis(4-methylsulfonylphenyl)-2-cyclobuten-1-one

To a solution of cyclobutenone from step 2 (530 mg) in benzene was added NBS (350 mg). The mixture was heated to reflux for 1.5 hr in the presence of a sun lamp, cooled to r.t. and the solvent evaporated. The resulting residue was purified by flash chromatography (silica gel; hexane/EtOAc (70:30)) to provide the title compound as a white solid, m.p. 212° C.

EXAMPLE 34

4-Methyl-2-(4-methylsulfonylphenyl)-3-phenyl-2-cyclobuten-1-one

Following the procedure describe in Example 6, step 3, but substituting N,N-dimethylpropionamide for N,N-dimethyl-2-(3-thienyl) propionamide, the title product was first purified by flash chromatography (silica gel; hexane/EtOAc (80:20)) and then the resulting solid was stirred vigorously in $Et_2O$ for 1 hr and filtered to afford the title compound as a pale yellow solid m.p. 121°–122° C.

EXAMPLE 35

4-Isopropyl-2-(4-methylsulfonylphenyl)-3-phenyl-2-cyclobuten-1-one

Following the procedure describe in Example 6, but substituting isovaleryl chloride for 3-thienyl acetyl chloride and omitting step 2, the title product was obtained as a white solid, m.p. 98° C.

EXAMPLE 36

4,4-Dichloro-3-methylene-1-(4-methylsulfonylphenyl)-2-phenyl-1-cyclobutene

Step 1: 4,4-Dichloro-3-methylene-1-(4-methylthiophenyl)-2-phenyl-1-cyclobutene

To a solution of Example 1 (810 mg) in THF (20 mL) at 0° C. was added Tebbe's reagent (0.5M, 5 mL) dropwise. The mixture was stirred at r.t. for 30 min., quenched with NaOH 0.5N at 0° C. and diluted with $Et_2O$. The organic phase was washed with $H_2O$, brine, dried ($MgSO_4$) and the solvents evaporated. Flash chromatography of the residue (silica gel; hexane/EtOAc (95:5)) provided the title compound as a yellow oil.

Step 2: 4,4-Dichloro-3-methylene-1-(4-methylsulfonylphenyl)-2-phenyl-1-cyclobutene Following the procedure describe in Example 2, but substituting sulfide from Step 1 for Example 1, the title product was obtained as a white solid, m.p. 124°–126° C.

EXAMPLE 37

Ethyl [4,4-dichloro-3-(4-methylsulfonylphenyl)-2-phenyl-2-cyclobuten-1-ylidene] acetate A solution of Example 2 (100 mg) and ethyl triphenylphosphoranylidene acetate (200 mg) in benzene (10 mL) was refluxed 4 hr, cooled to r.t. and the solvents evaporated. Flash chromatography of the residue (silica gel; hexane/EtOAc (70:30)) provided the title compound as a white solid (E/Z; 88:12), m.p. 118°–121° C.

EXAMPLE 38

[4,4-Dichloro-3-(4-methylsulfonylphenyl)-2-phenyl-2-cyclobuten-1-ylidene] ethanol To a solution of Example 37 (348 mg) in $CH_2Cl_2$ (25 mL) at −78° C. was added DIBAL (400 $\mu$L) dropwise. After 20 min., the reaction mixture was quenched with MeOH followed by a saturated $NH_4Cl$ sol. and then extracted with $Et_2O$. The organic phase was washed with $H_2O$, brine, dried ($MgSO_4$) and the solvents evaporated. The residue was first purified by flash chromatography (silica gel; hexane/EtOAc (70:30)) and then the resulting solid was stirred vigorously in hexane/$Et_2O$ for 1 hr and filtered to afford the title compound as a white solid (E/Z; 95:5), m.p. 194°–195° C.

EXAMPLE 39

3-Methylene-1-(4-methylsulfonylphenyl)-2-phenyl-1-cyclobutene

Step 1: 3-Methylene-1-(4-methylthiophenyl)-2-phenyl-1-cyclobutene

To a suspension of methyltriphenylphosphonium bromide (450 mg) in THF (10 mL) at r.t. was added potassium t-butoxide (1M, THF, 1.3 mL). After 30 min. the ketone (Example 4, step 1, 165 mg) was added and the mixture stirred for an additional 30 min. at r.t., quenched with a saturated $NH_4Cl$ sol. and diluted with $Et_2O$. The organic phase was washed with $H_2O$, brine, dried ($MgSO_4$) and the solvents evaporated.. Flash chromatography of the residue (silica gel; hexane/EtOAc (90:10)) provided the title compound as a white solid.

Step 2: 3-Methylene-1-(4-methylsulfonylphenyl)-2-phenyl-1-cyclobutene

Following the procedure describe in Example 2, but substituting sulfide from Step 1 for Example 1, the title product was obtained as a pale yellow foam; $^1$H NMR (300 MHz, $CDCl_3$): δ 3.03 (s, 3H), 3.37 (s, 2H), 4.81 (s, 1H), 5.09 (s, 1H), 7.3–7.5 (m, 5H), 7.65 (d, 2H), 7.84 (d,2H).

EXAMPLE 40

(E)-Ethyl [3-(4-methylsulfonylphenyl)-2-phenyl-2-cyclobuten-1-ylidene] acetate

Step 1: (E)-Ethyl [3-(4-methylthiophenyl)-2-phenyl-2-cyclobuten-1-ylidene] acetate A solution of cyclobutenone from Example 4, step 1 (600 mg) and ethyl triphenylphosphoranylidene acetate (1.6 g) in benzene (30 mL) was heated at reflux for 5 hr, cooled to r.t. and the solvent evaporated. The residue was first purified by flash chromatography (silica gel; hexane/EtOAc (90:10)). The major product was obtained as a solid which was stirred vigorously in hexane/$Et_2O$ for 1 hr and filtered to afford the title (E)-compound as a yellow solid (E/Z; 90:10)

Step 2: Ethyl [3-(4-methylsulfonylphenyl)-2-phenyl-2-cyclobuten-1-ylidene] acetate Following the procedure describe in Example 2, but substituting sulfide from Step 1 for Example 1, the title product was obtained as pale yellow solid (E/Z; 95:5), m.p. 183°–186° C.

EXAMPLE 41

(Z)-Ethyl [3-(4-methylsulfonylphenyl)-2-phenyl-2-cyclobuten-1-ylidene] acetate

Step 1: (Z)- Ethyl [3-(4-methylthiophenyl)-2-phenyl-2-cyclobuten-1-ylidene] acetate After the chromatography described in Example 40, Step 1, the fractions containing the (Z)-isomer as the major componant were evaporated and the resulting solid was stirred vigorously in hexane/$Et_2O$ for 1 hr and filtered to afford the title (Z)-product as a yellow solid.

Step 2: (Z)-Ethyl [3-(4-methylsulfonylphenyl)-2-phenyl-2-cyclobuten-1-ylidene] acetate Following the procedure describe in Example 2, but substituting sulfide from Step 1 for Example 1, the title product was obtained as white solid (E/Z; 10:90), m.p. 126°–128° C.

EXAMPLE 42 AND 43

(Z) and (E)-[3-(4-methylsulfonylphenyl)-2-phenyl-2-cyclobuten-1-ylidene]-2-propanol Step 1: Ethyl [3-(4-methylthiophenyl)-2-phenyl-2-cyclobuten-1-ylidene]-2-propanoate A solution of cyclobutenone from Example 4, step 1 (175 mg) and (carbethoxyethylidene)triphenylphosphorane(360 mg) in benzene (10 mL) was heated at reflux for 18 hr, cooled to r.t. and the solvent evaporated. The residue was first purified by flash chromatography (silica gel; hexane/EtOAc (90:10)) to afford the title product as an oil (E/Z; ≈50:50).

Step 2: Ethyl [3-(4-methylsulfonylphenyl)-2-phenyl-2-cyclobuten-1-ylidene]-2-propanoate Following the procedure describe in Example 2, but substituting sulfide from Step 1 for Example 1, the resulting residue was purified by flash chromatography (silica gel; hexane/EtOAc (70:30)) to afford the title compound as a white solid.

Step 3: (Z) and (E)-[3-(4-methylsulfonylphenyl)-2-phenyl-2-cyclobuten-1-ylidene]-2-propanol To a solution of ester from step 2 (440 mg) in $CH_2Cl_2$ (25 mL) at −78° C. was added DIBAL dropwise. After 30 min., the mixture was quenched with a saturated $NH_4Cl$ sol. and $Et_2O$. The organic phase was decanted, washed with $H_2O$, brine, dried ($MgSO_4$) and the solvents evaporated. The residue was purified by flash chromatography (silica gel; hexane/EtOAc (70:30 to 60:40)) to afford the title compounds as a white solid for the less polar (Z)-isomer (example 42), m.p. 135°–137° C., and as a yellow foam for the more polar (E)-isomer (example 43); $^1$H NMR (300 MHz, $CDCl_3$): δ 1.69 (s, 3H), 2.99 (s, 3H), 3.24 (s, 2H), 4.15 (s, 2H), 7.4 (m, 7H), 7.76 (d, 2H).

EXAMPLE 44

4,4-Dimethyl-3-methylene-1-(4-methylsulfonylphenyl)-2-phenyl-1-cyclobutene

Following the procedure describe in Example 39, but substituting Example 16 for Example 4, the resulting residue was purified by flash chromatography (silica gel; hexane/EtOAc (75:25)) to afford the title compound as a white solid, m.p. 110°–111° C.

EXAMPLE 45

4,4-Dimethyl-3-(4-methylsulfonylphenyl)-2-phenyl-2-cyclobuten-1-one oxime

A solution of Example 16 (1.63 g) and hydroxylamine hydrochloride (1.4 g) in pyridine (10 mL) was refluxed for 18 hr. The solvent was evaporated, the residue diluted with EtOAc and poured into HCl 1N. The organic phase was washed with HCl 1N, $H_2O$, brine, dried ($MgSO_4$) and the solvent evaporated. The resulting residue was purified by flash chromatography (silica gel; hexane/EtOAc (70:30 to 60:40)) to give the title compound as white solid, m.p. 217°–220° C.

EXAMPLE 46

4,4-Dimethyl-3-(4-methylsulfonylphenyl)-2-phenyl-2-cyclobuten-1-one t-butyloxime Following the procedure describe in Example 45, but substituting O-(t-butyl)hydroxylamine hydrochloride for hydroxylamine hydrochloride, the title products were obtained as the (E) and (Z) isomers; the less polar one as white solid, m.p. 125°–126° C. and the more polar isomer as an oil; $^1$H NMR (300 MHz, Ace-$d_6$): δ 1.25 (s, 9H), 1.58 (s, 6H), 3.14 (s, 3H), 7.36–7.39 (m, 3H), 7.65–7.68 (m, 2H), 7.75 (d, 2H), 7.92 (d, 2H).

EXAMPLE 47

4,4-Dimethyl-3-(4-methylsulfonylphenyl)-2-phenyl-2-cyclobuten-1-one methyloxime A solution of Example 16 (163 mg) and methoxylamine hydrochloride (83 mg) in pyridine (1.5 mL) and EtOH (1.5 mL) was heated at 110° C. for 18 hr. The solvents were evaporated, the residue diluted with EtOAc and HCl 0.2N. The organic phase was washed with brine, dried ($MgSO_4$) and the solvent evaporated. The resulting residue was purified by flash chromatography (silica gel; hexane/EtOAc (70:30)) to give the title compound as white solid, m.p. 156°–158° C.

EXAMPLE 48

4,4-Dimethyl-3-(4-methylsulfonylphenyl)-2-phenyl-2-cyclobuten-1-one benzyloxime Following the procedure describe in Example 47, but substituting O-benzylhydroxylamine hydrochloride for methoxylamine hydrochloride, the title product was obtained as a white solid, m.p. 119°–121° C.

EXAMPLE 49

1-N-Benzylimine-4,4-dimethyl-3-(4-methylsulfonylphenyl)-2-phenyl-2-cyclobutene A mixture of Example 16 (200 mg), benzylamine (134 μL) and p-TsOH (140 mg) in toluene (20 ml) was refluxed, with azeotropic removal of water, for 48 hr, cooled to r.t., washed with saturated $NaCHO_3$ sol., brine, dried ($MgSO_4$) and the solvent evaporated. The residue was purified by flash chromatography (silica gel; hexane/EtOAc (80:20)) to give the title product as a beige solid, m.p. 189°–190° C.

EXAMPLE 50

4,4-Dimethyl-3-(4-methylsulfonylphenyl)-2-phenyl-2-cyclobuten-1-one 3-picolyloxime To a solution of Example 45 (102 mg) in DMF (3 mL) was added $Cs_2CO_3$ (390 mg) and a solution of 3-picolylchloride hydrochloride (154 mg) in DMF (3 mL). The mixture was heated at 80° C. for 18 hr, diluted with EtOAc and $H_2O$. The aqueous phase was extracted with EtOAc, the combined organic phase was washed with brine, dried ($MgSO_4$) and the solvent evaporated. The resulting residue was purified by flash chromatography (silica gel; hexane/EtOAc (40:60)) to give the title compound as white foam; $^1$H NMR (300 MHz, Ace-$d_6$): δ 1.61 (s,6H), 3.17 (s, 3H), 5.22 (s, 2H), 7.36–7.41 (m, 4H), 7.69 (m, 2H), 7.85 (m, 3H), 7.98 (d, 2H), 8.52 (dd, 1H), 8.68 (br s, 1H).

EXAMPLE 51

4,4-Dimethyl-3-(4-methylsulfonylphenyl)-2-phenyl-2-cyclobuten-1-one 2-picolyloxime Following the procedure described in Example 50 but substituting 2-picolylchloride hydrochloride for 3-picolylchloride hydrochloride, the title compound was obtained as a white foam; $^1$H NMR (300 MHz, Ace-$d_6$): δ 1.68 (s,6H), 3.17 (s, 3H), 5.27 (s, 2H), 7.26 (m, 1H), 7.37 (m, 3H), 7.50 (d, 1H), 7.69 (m, 2H),7.8 (dt, 1H), 7.90 (d, 2H), 8.0 (d, 2H), 8.55 (dd, 1H).

EXAMPLE 52

4,4-Dimethyl-3-(4-methylsulfonylphenyl)-2-phenyl-2-cyclobuten-1-one (3-carbomethoxy)benzyl oxime Following the procedure described in Example 50 but substituting methyl 3-bromomethylbenzoate for 3-picolylchloride hydrochloride, the title compound was obtained as an oil; $^1$H NMR (300 MHz, Ace-$d_6$): δ 1.64 (s,6H), 3.17 (s, 3H), 3.89 (s, 3H), 5.26 (s, 2H), 7.39 (m, 3H), 7.55 (t, 1H), 7.70 (m, 3H),7.85 (d, 2H), 7.95 (dd, 1H), 8.03 (d, 2H), 8.16 (br s, 1H).

EXAMPLE 53

4,4-Dimethyl-3-(4-methylsulfonylphenyl)-2-phenyl-2-cyclobuten-1-one (3-carboxy)benzyl oxime A solution of methyl ester from Example 52 (90 mg) in THF (2 mL) and MeOH (1 mL) was treated with LiOH (2N, 276 μL ). The mixture was heated at reflux for 18 hr, cooled to r.t. and diluted with EtOAc and HCl 1N. The organic phase was washed with brine, dried ($MgSO_4$) and the solvent evaporated to give the title compound as white foam; $^1$H NMR (300 MHz, Ace-$d_6$): δ 1.64 (s,6H), 3.17 (s, 3H), 5.26 (s, 2H), 7.39 (m, 3H), 7.51 (t, 1H), 7.70 (m, 3H),7.86 (d, 2H), 8.0 (m, 3H), 8.15 (br s, 1H).

EXAMPLE 54

3-(4-Methylsulfonylphenyl)-2-phenyl-2-cyclobuten-1-one oxime

Following the procedure describe in Example 45, but substituting Example 4 for Example 16, the title product was obtained as a white solid, m.p. 146.5°–147.5° C.

EXAMPLE 55

3-(4-Methylsulfonylphenyl)-2-phenyl-2-cyclobuten-1-one t-butyloxime

Following the procedure describe in Example 45, but substituting Example 4 for Example 16 and O-(t-butyl) hydroxylamine hydrochloride for hydroxylamine hydrochloride, the title product was obtained as a white solid, m.p. 150°–151.5° C.

EXAMPLE 56

4,4-Dimethyl-3-(4-methylsulfonylphenyl)-2-phenyl-2-cyclobuten-1-one methyloxime

Following the procedure describe in Example 45, but substituting Example 4 for Example 16, and methoxylamine hydrochloride for hydroxylamine hydrochloride, the title product was obtained as a white solid, m.p. 146°–147° C.

EXAMPLE 57

3-(4-Methylsulfonylphenyl)-2-phenyl-2-cyclobuten-1-one benzyloxime

Following the procedure describe in Example 47, but substituting Example 4 for Example 16 and O-benzylhydroxylamine hydrochloride for methoxylamine hydrochloride, the title product were obtained as a white solid, m.p. 148.5°–149.5° C.

EXAMPLE 58

4,4-Dimethyl-2-(4-methylsulfonylphenyl)-3-phenyl-2-cyclobuten-1-one t-butyloximes Following the procedure describe in Example 46, but substituting Example 30 for Example 16, the separable stereoisomers of the title products were obtained as white solids: (a) the less polar isomer, m.p. 184°–185° C. and (b) the more polar isomer, m.p. 135°–136° C.

EXAMPLE 59

4,4-Dimethyl-2-(4-methylsulfonylphenyl)-3-phenyl-2-cyclobuten-1-one benzyloxime

Following the procedure describe in Example 48, but substituting Example 30 for Example 16, the title product was obtained as a white solid, m.p. 56°–61° C.

EXAMPLE 60

1-(4-Methylsulfonylphenyl)-2-phenyl-1-cyclobutene

Step 1: 1-(4-Methylthiophenyl)-4-phenyl-1,4-butadione

To a solution of 3-benzoylpropionic acid (10 g) in $CH_2Cl_2$ (50 mL) at 0° C., was added oxalyl chloride (5.4 mL) and 5 drops of DMF. The mixture was stirred at 0° C. for 15 min., at r.t. for 2 hr and the solvents evaporated. The crude oil was dissolved in $CH_2Cl_2$ (50 mL) at 0° C. and aluminium chloride (7.5 g) was added followed by thioanisole (6.6 g). After 3 hr at 0° C., the reaction mixture was poured into ice and extracted with ether. The organic phase was washed with $H_2O$, brine, dried ($MgSO_4$) and the solvents evaporated. The residue was purified by flash chromatography (silica gel; hexane/EtOAc (75:25)) to afford the title compounds as an oil.

Step 2: 1-(4-Methylthiophenyl)-2-phenyl-1-cyclobutene

To a solution of dione from step 1 (500 mg) in THF (18 mL) at −40° C. was added $TiCl_4$ (0,93 mL) dropwise followed after 5 min., by Zn dust (1.1 g). The mixture was stirred at −40° C. for 1 hr, at r.t. for 1.5 hr, poured into ice and extracted with ether. The organic phase was washed with $H_2O$, brine, dried ($MgSO_4$) and the solvents evaporated. The residue was purified by flash chromatography (silica gel; hexane/EtOAc (80:20)) to give the title product as a colorless oil.

Step 3: 1-(4-Methylsulfonylphenyl)-2-phenyl-1-cyclobutene

Following the procedure describe in Example 2, but substituting 1-(4-methylthiophenyl)-2-phenyl-1-cyclobutene from Step 2 for Example 1, the title compound was purified by flash chromatography (silica gel; hexane/EtOAc (80:20)) to give a white solid, m.p. 73°–75° C.

EXAMPLE 61

1,4,4-Trimethyl-3-(4-methylsulfonylphenyl)-2-phenyl-2-cyclobuten-1-ol

To a solution of Example 16 (60 mg) in THF (1 mL) at −20° C., was added methyl magnesium bromide (3M, ether, 185 μL). The mixture was stirred at −20° C. for 1.5 hr, quenched with $H_2O$, and diluted with EtOAc. The organic phase was washed with $H_2O$, brine, dried ($MgSO_4$) and the solvents evaporated. The residue was purified by flash chromatography (silica gel; hexane/EtOAc (80:20)) to give the title compounds as a white solid, m.p. 114°–115° C.

EXAMPLE 62

4,4-Dimethyl-3-(4-methylsulfonylphenyl)-2-phenyl-2-cyclobuten-1-ol

To a solution of Example 14 (100 mg) in THF (1 mL) at 0° C., was added LAH (1M, THF, 920 μL). The mixture was stirred at 0° C. for min., quenched with $H_2O$, and diluted with EtOAc. The organic phase was washed with HCl 1N, brine, dried ($MgSO_4$) and the solvents evaporated. The residue was purified by flash chromatography (silica gel; hexane/EtOAc (70:30)) to give the title compound as a white solid, m.p. 79°–81° C.

EXAMPLE 63

4,4-Dimethyl-1-methoxy-3-(4-methylsulfonylphenyl)-2-phenyl-2-cyclobutene

To a solution of Example 62 (70 mg) in $CH_2Cl_2$ (1 mL) at r.t., was added silver oxide (100 mg) and MeI (1 mL). The mixture was stirred reflux for 18 hr, cooled to r.t., filtered through celite® and the solvents evaporated. The residue was purified by flash chromatography (silica gel; hexane/EtOAc (85:15)) to give the title product as a white solid, m.p. 130°–132° C.

EXAMPLE 64

4,4-Dimethyl-1-acetoxy-3-(4-methylsulfonylphenyl)-2-phenyl-2-cyclobutene

To a solution of Example 62 (150 mg) in $CH_2Cl_2$ (3 mL) at r.t., was added pyridine (370 mL), $Ac_2O$ (215 μL) and DMAP (5 mg). The mixture was stirred at r.t. for 2 hr and diluted with EtOAc and $H_2O$. The organic phase was washed with HCl 1N, brine, dried ($MgSO_4$) and the solvents evaporated. The residue was purified by flash chromatography (silica gel; hexane/EtOAc (70:30)) to give the title compound as a white solid, m.p. 60°–61° C.

EXAMPLE 65

4,4-Dimethyl-1-pivaloxy-3-(4-methylsulfonylphenyl)-2-phenyl-2-cyclobutene

To a solution of Example 62 (100 mg) in $CH_2Cl_2$ (1.5 mL) at r.t., was added diisopropylethylamine (105 μL) and pivaloyl chloride (70 μL). The mixture was stirred at r.t. for 1.5 hr and the solvents evaporated. The residue was purified by flash chromatography (silica gel; hexane/EtOAc (80:20)) to give the title compound as a yellow solid, m.p. 66°–67° C.

EXAMPLE 66

4,4-Dimethyl-1-fluoro-3-(4-methylsulfonylphenyl)-2-phenyl-2-cyclobutene

To diethylaminosulfur trifluoride (930 μL) at 0° C., was added Example 62 (250 mg) portionwise. The mixture was warmed to r.t. 10 min., diluted with $CHCl_3$, cooled to 0° C. and quenched carefully with saturated $NaCHO_3$ sol.. The organic phase was washed with a saturated $NaCHO_3$ sol., brine, dried ($MgSO_4$) and the solvents evaporated. The residue was purified by flash chromatography (silica gel; hexane/EtOAc (80:20)) to give the title compound as a white solid, m.p. 79°–81.5° C.

EXAMPLE 67

4,4-Dimethyl-3-(4-methylsulfonylphenyl)-2-phenyl-2-cyclobuten-1-ol N-phenylcarbamate To a solution of Example 62 (150 mg) in toluene (2.3 mL) at r.t., was added diisopropylethylamine (160 μL) and phenylisocyanate (100 μL ). The mixture was refluxed for 4 hr, cooled to r.t. and diluted with EtOAc and $H_2O$. The organic phase was washed with HCl 1N, brine, dried ($MgSO_4$) and the solvents evaporated. The residue was purified by flash chromatography (silica gel; hexane/EtOAc (80:20 to 60:40)) to give the title compound as a white solid, m.p. 85.5°–87° C.

EXAMPLE 68

4,4-Dimethyl-3-(4-methylsulfonylphenyl)-2-phenyl-2-cyclobuten-1-one (ethylenedithioacetal)

To a solution of Example 16 (300 mg) in $CH_2Cl_2$ (5 mL) at r.t., was added 1,2-ethanedithiol (115 mL) and boron trifluoride etherate (25 μL). The mixture was stirred at r.t. for 1.5 hr, diluted with EtOAc and NaOH 1N. The organic phase was washed with NaOH 1N, brine, dried ($MgSO_4$) and the solvents evaporated. The residue was purified by flash chromatography (silica gel; hexane/EtOAc (80:20)) to give the title compound as a white solid, m.p. 145°–146.5° C.

EXAMPLE 69

4,4-Dimethyl-2-(4-methylsulfonylphenyl)-3-phenyl-2-cyclobuten-1-ol

Following the procedure described in Example 62 but substituting Example 30 for Example 16, the residue was purified by flash chromatography (silica gel; hexane/EtOAc (60:40 to 50:50)) to give the title compound as a white foam, $^1H$ NMR (300 MHz, Ace-$d_6$-$D_2O$): δ. 1.24 (s, 3H), 1.44 (s, 3H), 3.12 (s, 3H), 4.62 (s, 1H), 7.36–7.44 (m, 3H), 7.48–7.52 (m, 2H), 7.73 (dm, 2H), 7.86 (dm, 2H).

EXAMPLE 70

4,4-Dimethyl-1-methoxy-2-(4-methylsulfonylphenyl)-3-phenyl-2-cyclobutene

Following the procedure described in Example 63 but substituting Example 69 for Example 62, the residue was purified by flash chromatography (silica gel; hexane/EtOAc (67:33)) to give the title compound as a white solid, m.p. 120°–121° C.

EXAMPLE 71

4,4-Dimethyl-1-acetoxy-2-(4-methylsulfonylphenyl)-3-phenyl-2-cyclobutene

Following the procedure described in Example 64 but substituting for Example 69 for Example 62, the residue was purified by flash chromatography (silica gel; hexane/EtOAc (60:40)) to give the title compound as a white solid, m.p. 156°–158° C.

STARTING MATERIALS

PREPARATION OF 1,2-DIARYLETHYLENES (E)-1-(Methylthio)-4-(2-phenylethenyl)benzene Method 1

To a cooled (0° C.) suspension of benzyltriphenylphosphonium chloride (9.2 g) in THF (165 mL) was added n-BuLi (2.5M, 19 mL) dropwise. After 15 min., a solution of 4-methylthiobenzaldehyde (4.37 g) in THF (20 mL) was added. The mixture was stirred at 0° C. for 1.5 hr, diluted with EtOAc, washed with $H_2O$, brine, dried ($MgSO_4$) and the solvents evaporated. The resulting solid was recrystallized in ether/pentane to provide the desired (E) olefin as a white solid.

Method 2

To a solution of 4-methylthiobenzaldehyde (50 g) in THF (500 mL) at −78° C. was added benzylmagnesium chloride (2M, THF, 200 mL) dropwise. The mixture was stirred at −40° C. for 1.5 hr, poured into ice and HCl 1N and extracted with EtOAc (3×). The combined organic phase was washed with $H_2O$, brine, dried ($MgSO_4$) and the solvents evaporated. The crude residu was diluted with toluene (1.0 L) and TsOH (3.9 g) was added. The mixture was refluxed with azeotropic removal of water for 18 hr, cooled to r.t., washed with saturated $NaCHO_3$ sol., brine, dried ($MgSO_4$) and the solvent evaporated. The resulting solid was stirred vigorously in $Et_2O$ for 2 hr and then filtered to afford the title compound as a white solid.

(E)-1-(Methylthio)-4-[2-(4-methylthiophenyl)ethenyl]benzene

Step 1: 4-Methylthiobenzyltriphenylphosphonium chloride

A solution of 4-methylthiobenzyl chloride (3.1 g) and triphenylphosphine (4.72 g) was heated in toluene (35 mL) at reflux for 18 hr. The mixture was cooled to 0° C. and filtered. The resulting solid was used as such in the next step.

Step 2: (E)-1-(Methylthio)-4-[2-(4-methylthiophenyl)ethenyl]benzene

Following the procedure as describe in method 1, but sustituting 4-methylthiobenzyltriphenylphosphonium chloride for benzyltriphenylphosphonium chloride, the desired residue was purified by flash chromatography (silica gel; hexane/EtOAc (90:10)) and recrystallisation from hexane.

(E)-1-(Methylthio)-4-[2-(4-fluorophenyl)ethenyl]benzene

Method 3

To a solution of 4-fluorostyrene (2.0 g) in DMF (40 mL) at r.t. was added 4-bromothioanisole (3.66 g), LiCl (1.09 g), LiOAc-$2H_2O$ (4.24 g), $Bu_4NCl$ (9.3 g) and $Pd(OAc)_2$ (107 mg). The mixture was heated at 115° C. for 18 hr, cooled to r.t., quenched with a $NH_4OAc$ sol. and extracted with EtOAc. The organic phase was washed with $H_2O$, saturated $NaCHO_3$ sol., brine, dried ($MgSO_4$) and the solvents evaporated to give the title product.

(E)-1-(Methylthio)-4-[2-(3-fluorophenyl)ethenyl]benzene

Method 4

Step 1: 4-Methylthiostyrene

To a suspension of methyltriphenylphosphonium bromide (1.76 g) in THF (15 mL) at r.t. was added potassium t-butoxide (1M, THF, 6.6 mL). After 30 min., 4-methylthiobenzaldehyde (500 mg) was added and the mixture stirred for an additional 60 min. at r.t., quenched with a saturated $NH_4Cl$ sol. and diluted with $Et_2O$. The organic phase was washed with $H_2O$, brine, dried ($MgSO_4$) and the solvents evaporated to provide the title compound as a yellow oil.

Step 2: (E)-1-(Methylthio)-4-[2-(3-fluorophenyl)ethenyl] benzene

Following the procedure describe in Method 3, but substituting4-methylthiostyrene and 1-bromo-3-fluorobenzene for 4-fluorostyrene and 4-bromothioanisole, the title product was obtained as an off-white solid.

(E)-1-(Methylthio)-4-[2-(3 ,5-difluorophenyl)ethenyl] benzene

Following the procedure describe in Method 3, but substituting 4-methylthiostyrene (from method 4, step 1) and 1-bromo-3,5-difluorobenzene for 4-fluorostyrene and 4-methylthioanisole, the title product was obtained after flash chromatography (silica gel; toluene/hexane (50:50)) as an orange oil.

(E)-1-(Methylthio)-4-[2-(3,4-difluorophenyl)ethenyl] benzene

Method 5

Step 1: 3,4-Difluoro-N-methoxy-N-methyl benzamide

To a solution of 3,4-difluorobenzoyl chloride (5.25 g) in chloroform (30 mL) at 0° C. was added N,O-dimethylhydroxylamine hydrochloride (3.2 g) followed by pyridine (5.8 mL) dropwise. The mixture was stirred at r.t. for 2 hr, diluted with EtOAc, washed with HCl 1N, with $H_2O$, saturated $NaCHO_3$ sol., brine, dried ($MgSO_4$) and the solvents evaporated to give the title product.

Step 2: 1-(3,4-Difluorophenyl)-2-(4-methylthiophenyl)-1-ethanone

To a cold (0° C.) solution of amide from step 1(400 mg) in THF (20 mL) was added 4-methylthiobenzylmagnesium chloride (*J. Org. Chem.* 42, 1914, 1977). The mixture was stirred at 0° C. for 3 hr, quenched with $NH_4OAc$ sol. and extracted with EtOAc. The organic phase was washed with $H_2O$, brine, dried ($MgSO_4$) and the solvents evaporated. The title product was obtained after flash chromatography (silica gel; toluene/EtOAc (98:2)).

Step 3: 1-(3,4-Difluorophenyl)-2-(4-methylthiophenyl) ethanol

To a solution of ketone from step 2 (4.8 g) in THF (60 mL) at 0° C., was added LAH (1M, THF, 52 mL) dropwise. The mixture was stirred 30 min., quenched with HCl 2N, diluted with EtOAc, washed with HCl 1N, $H_2O$, brine, dried ($MgSO_4$) and the solvents evaporated. The residue was purified by flash chromatography (silica gel; hexane/EtOAc (90:10)) to give the title product as a colorless oil.

Step 4: (E)-1-(Methylthio)-4-[2-(3,4-difluorophenyl) ethenyl]benzene

The alcohol from step 3 (3.78 g) was dissolved in toluene (45 mL) and p-TsOH (260 mg) was added. The mixture was refluxed with azeotropic removal of water for 18 hr, cooled to r.t., washed with saturated $NaCHO_3$ sol., brine, dried ($MgSO_4$) and the solvent evaporated. The residue was purified by flash chromatography (silica gel; hexane/EtOAc (95:5)) to give the title product as a yellow oil.

PREPARATION OF 1,2-DIARYLACETYLENES 1-(Methylthio)-4-(phenylethynyl)benzene

Method 6

To a solution of 4-bromothioanisole (38.5 g) in $Et_3N$ (65 mL) was added phenyl acetylene (25 mL), $PdBr_2(PPh_3)_2$ (2 g) and CuI (2 g). The mixture was heated at 75° C. for 24 hr then another portion of phenyl acetylene (10 mL), $PdBr_2(PPh_3)_2$ (0.5 g) and CuI (0.5 g) was added. After 48 hr, the mixture was cooled to r.t., filtered through a pad of Celite® and silica gel and the solvents evaporated. The residue was stirred vigorously in hexane for 3 hr and filtered to afford the title compound as a white solid; $^1H$ NMR (300 MHz, $CDCl_3$): δ 2.52 (s, 3H), 7.26 (d, 2H), 7.35 (m, 3H), 7.42 (d, 2H), 7.5 (dd, 2H).

1-(Methylthio)-4-(4-fluorophenylethynyl)benzene

Following the procedure as describe in method 6 but substituting 4-fluorophenyl acetylene for phenylacetylene, the title product was obtained as a colorless oil; $^1H$ NMR (300 MHz, Ace-d6): δ 2.48 (s, 3H), 7.05 (t, 2H), 7.15 (d, 2H), 7.4 (d, 2H), 7.5 (q, 2H).

1-(Methylsulfonyl)-4-(phenylethynyl)benzene

Method 7

To a solution of 1-(methylthio)-4-(phenylethynyl)benzene (method 6, 14 g) in $CHCl_3$ (300 mL) at 0° C. was added m-chloroperbenzoic acid (80%, 29 g) portionwise. The mixture was stirred at 0° C. 30 min, at r.t. for 30 min. and then $Ca(OH)_2$ (14 g) was added. After 1 hr, the heterogeneous mixture was filtered and the solvent evaporated. The resulting solid residue was stirred vigorously in hexane for 1 hr and then filtered to afford the title compound as a white solid; $^1H$ NMR (300 MHz, $CDCl_3$): δ 3.17 (s, 3H), 7.42 (m, 3H), 7.57 (m, 2H), 7,78 (d, 2H), 7.98 (d, 2H).

What is claimed is:

1. A compound of formula I:

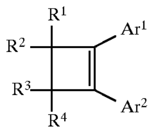

I or a pharmaceutically acceptable salt thereof, wherein $R^1$, $R^2$, $R^3$and $R^4$ are each independently selected from the group consisting of (a) H, (b) halogen, (c) hydroxy, (d) $C_{1-6}$alkyl, (e) $C_{2-6}$alkenyl, (f) $C_{2-6}$alkynyl, (g) $C_{1-6}$alkoxy, (h) hydroxy $C_{1-6}$alkyl, (i) $C_{1-6}$alkylthio, (j) CN, (k) $COR^5$, (l) $OCOR^6$, (m) $OCONHR^7$, or (n) a mono-, di- or tri-substituted phenyl, wherein the substituents are each independently $R^{11}$ or $R^1$ and $R^2$ or $R^3$ and $R^4$ are joined together with the carbon atom to which they are attached to form C=O, or $R^1$ and $R^2$ or $R^3$ and $R^4$ are joined together with the carbon atom to which they are attached to form C=S, or $R^1$ and $R^2$ or $R^3$ and $R^4$ are joined together with the carbon atom to which they are attached to form $C{=}CR^8R^9$, or $R^1$ and $R^2$ or $R^3$ and $R^4$ are joined together with the carbon atom to which they are attached to form $C{=}NR^{10}$, or $R^1$ and $R^2$ or $R^3$ and $R^4$ are joined together with the carbon atom to which they are attached to form a saturated monocyclic ring of 3,4,5,6 or 7 carbon atoms, $Ar^1$ is mono-substituted phenyl or naphthyl wherein the substituent is $R^{12}$;

$Ar^2$ is mono-, di- or tri-substituted phenyl, wherein the substituents are each independently $R^{11}$.

$R^5$ is (a) H, (b) $C_{1-6}$alkyl, or (c) $C_{1-6}$alkoxy;

$R^6$ is (a) $C_{1-6}$alkyl, (b) $C_{1-6}$alkoxy, or (c) mono-, di- or tri-substituted phenyl or pyridyl, wherein the substituents are each independently $R^{11}$;

$R^7$ is (a) H, (b) $C_{1-6}$alkyl, or (c) mono-, di- or tri-substituted phenyl or pyridyl, wherein the substituents are each independently $R^{11}$;

$R^8$ and $R^9$ are each independently (a) H, (b) hydroxy$C_{1-6}$alkyl, (c) $C_{1-6}$alkyl, (d) CN, or (e) $COR^5$;

$R^{10}$ is (a) hydroxy, (b) $C_{1-6}$alkoxy, (c) $C_{1-6}$alkyl, or (d) substituted $C_{1-6}$alkyl or $C_{1-6}$alkoxy, wherein the substituent is a mono-, di- or tri-substituted phenyl or pyridyl and the substituents on the phenyl or pyridyl are $R^{11}$;

$R^{11}$ is (a) H, (b) halogen, (c) $C_{1-6}$alkyl, (d) hydroxy, (e) hydroxy $C_{1-6}$alkyl, (f) $C_{1-6}$alkoxy, (g) $CF_3$, (h) CN, (i) $COR^5$, or (j) $S(O)_nR^{13}$ wherein n is 0, 1 or 2;

$R^{12}$ is $S(O)_nR^{13}$ or $S(O)_2NHR^{14}$;

$R^{13}$ is $C_{1-6}$alkyl;

$R^{14}$ is H or $C_{1-6}$alkyl.

2. A compound according to claim 1 wherein $R^1$, $R^2$, $R^3$and $R^4$ are each independently selected from the group consisting of (a) H, (b) halogen, (c) hydroxy, (d) $C_{1-6}$alkyl, (e) $C_{2-6}$alkenyl, (f) $C_{2-6}$alkynyl, (g) $C_{1-6}$alkoxy, (h) hydroxy $C_{1-6}$alkyl, (i) $C_{1-6}$alkylthio, (j) CN, (k) $COR^5$, (l) $OCOR^6$, (m) $OCONHR^7$, or (n) mono-, di- or tri-substituted phenyl, wherein the substituents are each independently $R^{11}$ or $R^1$ and $R^2$ or $R^3$ and $R^4$ are joined together with the carbon atom to which they are attached to form C=O, or $R^1$ and $R^2$ or $R^3$ and $R^4$ are joined together with the carbon atom to which they are attached to form $C{=}CR^8R^9$, or $R^1$ and $R^2$ or $R^3$ and $R^4$ are joined together with the carbon atom to which they are attached to form $C{=}NR^{10}$, or $R^1$ and $R^2$ or $R^3$ and $R^4$ are joined together with the carbon atom to which they are attached to form a saturated monocyclic ring of 3,4,5 or 6 carbon atoms, $Ar^1$ is mono-substituted phenyl wherein the substituent is $R^{12}$;

$R^5$ is (a) H, (b) $C_{1-6}$alkyl, or (c) $C_{1-6}$alkoxy;

$R^6$ is (a) $C_{1-6}$alkyl, or (b) $C_{1-6}$alkoxy;

$R^7$ is (a) H, (b) $C_{1-6}$alkyl, or (c) mono-, di- or tri-substituted phenyl, wherein the substituents are each independently $R^{11}$;

$R^8$ and $R^9$ are each independently (a) H, (b) hydroxy$C_{1-6}$alkyl, (c) $C_{1-6}$alkyl, or (d) $COR^5$;

$R^{10}$ is (a) hydroxy, (b) $C_{1-6}$alkoxy, or (c) substituted $C_{1-6}$alkyl or $C_{1-6}$alkoxy, wherein the substituent is a mono-, di- or tri-substituted phenyl or pyridyl and the substituents on the phenyl or pyridyl are $R^{11}$;

$R^{11}$is (a) H, (b) halogen, (c) $C_{1-6}$alkyl, (d) hydroxy, (e) hydroxy$C_{1-6}$alkyl, (f) $C_{1-6}$alkoxy, (g) $CF_3$, (h) CN, (i) $COR^5$, or (j) $S(O)_nCH_3$ wherein n is 0, 1 or 2;

$R^{12}$ is $S(O)_nCH_3$ or $S(O)_2NH_2$.

3. A compound according to claim 2 of formula Ic

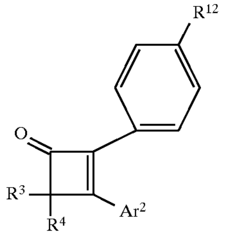

Ic wherein $R^3$ and $R^4$ are each independently selected from the group consisting of
(a) H,
(b) halogen,
(c) hydroxy,
(d) $C_{1-4}$alkyl,
(e) $C_{2-4}$alkenyl,
(f) $C_{1-4}$alkoxy,
(g) hydroxy $C_{1-4}$alkyl,
(h) CN,
(i) $COR^5$,
(j) $OCOR^6$,
(k) $OCONHR^7$, or
(h) a mono-, di- or tri-substituted phenyl, wherein the substituents are each independently $R^{11}$, or $R^3$ and $R^4$ are joined together with the carbon atom to which they are attached to form $C{=}CR^8R^9$, or $R^3$ and $R^4$ are joined together with the carbon atom to which they are attached to form a saturated monocyclic ring of 3,4,5 or 6 carbon atoms, $Ar^2$ is mono-, di- or tri-substituted phenyl, wherein the substituents are each independently $R^{11}$;

$R^5$ is
(a) H,
(b) $C_{1-4}$alkyl, or
(c) $C_{1-4}$alkoxy;

$R^6$ is
(a) $C_{1-4}$alkyl, or
(b) $C_{1-4}$alkoxy;

$R^7$ is
(a) H,
(b) $C_{1-4}$alkyl, or
(c) mono-, di- or tri-substituted phenyl, wherein the substituents are each independently $R^{11}$;

$R^8$ and $R^9$ are each independently
(a) H,
(b) hydroxy$C_{1-4}$alkyl,
(c) $C_{1-4}$alkyl;

$R^{11}$ is
(a) H,
(b) halogen,
(c) $C_{1-4}$alkyl,
(d) hydroxy,
(e) hydroxy $C_{1-4}$alkyl,
(f) $C_{1-4}$alkoxy,
(g) $CF_3$,
(h) CN,
(i) $S(O)_nCH_3$ wherein n is 0, 1 or 2;

$R^{12}$ is $S(O)_2CH_3$ or $S(O)_2NH_2$.

4. A compound according to claim 3 wherein $R^3$ and $R^4$ are each independently selected from the group consisting of
(a) H,
(b) halogen,
(c) hydroxy,
(d) $C_{1-4}$alkyl,
(e) $C_{2-4}$alkenyl,
(f) hydroxy $C_{1-4}$alkyl, or
(g) a mono-, di- or tri-substituted phenyl, wherein the substituents are each independently $R^{11}$, or $R^3$ and $R^4$ are joined together with the carbon atom to which they are attached to form $C{=}CR^8R^9$, or $R^3$ and $R^4$ are joined together with the carbon atom to which they are attached to form a saturated monocyclic ring of 3,4,5 or 6 carbon atoms, $R^8$ and $R^9$ are each independently
(a) H,
(b) hydroxyalkyl,
(c) $C_{1-4}$alkyl;

$R^{11}$ is
(a) H,
(b) halogen,
(c) $C_{1-4}$alkyl,
(d) hydroxy,
(e) hydroxy $C_{1-4}$alkyl,
(f) $C_{1-4}$alkoxy;
(g) $S(O)_nCH_3$ wherein n is 0, 1 or 2;

$R^{12}$ is $S(O)_2CH_3$ or $S(O)_2NH_2$.

5. A compound according to claim 4 wherein $R^3$ and $R^4$ are each independently selected from $C_{1-4}$alkyl;

$Ar^2$ is mono-, di-, or tri-substituted phenyl wherein the substituents are each independently $R^{11}$;

$R^{11}$ is
(a) H,
(b) halogen,
(c) $C_{1-4}$alkyl, $R^{12}$ is $S(O)_2CH_3$ or $S(O)_2NH_2$.

6. A compound according to claim 1 of Formula Ib

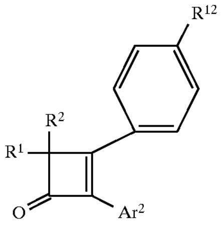

Ib wherein $R^1$ and $R^2$ are each independently selected from the group consisting of
(a) H,
(b) halogen,
(c) hydroxy,
(d) $C_{1-4}$alkyl,
(e) $C_{2-4}$alkenyl,
(f) $C_{2-4}$alkynyl,
(g) $C_{1-4}$alkoxy,
(h) hydroxy $C_{1-4}$alkyl,
(i) $C_{1-4}$alkylthio,
(j) CN,
(k) $COR^5$,
(I) $OCOR^6$,
(m) $OCONHR^7$, or
(n) a mono-, di- or tri-substituted phenyl, wherein the substituents are each independently $R^{11}$, or $R^1$ and $R^2$ are joined together with the carbon atom to which they are attached to form $C{=}CR^8R^9$, or $R^1$ and $R^2$ are joined together with the carbon atom to which they are attached to form a saturated monocyclic ring of 3,4,5 or 6 carbon atoms, $Ar^2$ is mono-, di- or tri-substituted phenyl, wherein the substituents are each independently $R^{11}$;

$R^5$ is
(a) H,
(b) $C_{1-4}$alkyl, or
(c) $C_{1-4}$alkoxy;

$R^6$ is
(a) $C_{1-4}$alkyl, or
(b) $C_{1-4}$alkoxy;

$R^7$ is
(a) H,
(b) $C_{1-4}$alkyl, or
(c) mono-, di- or tri-substituted phenyl, wherein the substituents are each independently $R^{11}$;

$R^8$ and $R^9$ are each independently
(a) H,
(b) hydroxy$C_{1-4}$alkyl,
(c) $C_{1-4}$alkyl, or
(d) $COR^5$;

$R^{11}$ is
(a) H,
(b) halogen,
(c) $C_{1-4}$alkyl,
(d) hydroxy,
(e) hydroxy $C_{1-4}$alkyl,
(f) $C_{1-4}$alkoxy,
(g) $CF_3$,
(h) CN,
(i) $COR^5$, or
(j) $S(O)_nCH_3$ wherein n is 0, 1 or 2;

$R^{12}$ is $S(O)_2CH_3$ or $S(O)_2NH_2$.

7. A compound according to claim 6 wherein $R^1$ and $R^2$ are each independently selected from the group consisting of
(a) H,
(b) halogen,
(c) hydroxy,
(d) $C_{1-4}$alkyl,
(e) $C_{2-4}$alkenyl,
(f) $C_{2-4}$alkynyl,
(g) $C_{1-4}$alkoxy,
(h) hydroxy $C_{1-4}$alkyl,
(i) $C_{1-4}$alkylthio,
(j) CN, or
(k) a mono-, di- or tri-substituted phenyl, wherein the substituents are each independently $R^{11}$ $Ar^2$ is mono-, di- or tri-substituted phenyl, wherein the substituents are each independently $R^{11}$;

$R^{11}$ is
(a) H,
(b) halogen,
(c) $C_{1-4}$alkyl,
(d) hydroxy,
(e) hydroxy $C_{1-4}$alkyl,
(f) $C_{1-4}$alkoxy,
(g) $S(O)_nCH_3$ wherein n is 0, 1 or 2;

$R^{12}$ is $S(O)_2CH_3$ or $S(O)_2NH_2$.

8. A compound according to claim 7 wherein $R^1$ and $R^2$ are each independently selected from the group consisting of
(a) $C_{1-4}$alkyl, or
(b) a mono-, di- or tri-substituted phenyl, wherein the substituents are each independently $R^{11}$ $Ar^2$ is mono-, di- or tri-substituted phenyl, wherein the substituents are each independently $R^{11}$;

$R^{11}$ is
(a) H,
(b) halogen,
(c) $C_{1-4}$alkyl, $R^{12}$ is $S(O)_2CH_3$ or $S(O)_2NH_2$.

9. A compound of Formula Ig'

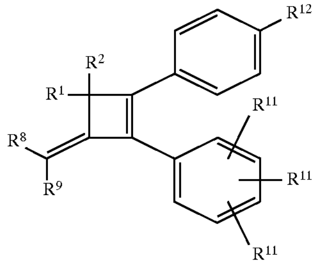

Ig' wherein $R^1$ and $R^2$ are each independently selected from the group consisting of
(a) H,
(b) halogen,
(c) hydroxy,
(d) $C_{1-4}$alkyl,
(e) $C_{2-4}$alkenyl,
(f) $C_{2-4}$alkynyl,
(g) $C_{1-4}$alkoxy,
(h) hydroxy $C_{1-4}$alkyl,
(i) $C_{1-4}$alkylthio,
(j) CN,
(k) $COR^5$,
(l) $OCOR^6$,
(m) $OCONHR^7$, or
(n) a mono-, di- or tri-substituted phenyl, wherein the substituents are each independently $R^{11}$;

$R^5$ is
(a) H,
(b) $C_{1-4}$alkyl, or
(c) $C_{1-4}$alkoxy;

$R^6$ is
(a) $C_{1-4}$alkyl, or
(b) $C_{1-4}$alkoxy;

$R^7$ is
(a) H,
(b) $C_{1-4}$alkyl, or
(c) mono-, di- or tri-substituted phenyl, wherein the substituents are each independently $R^{11}$;

$R^8$ and $R^9$ are each independently
(a) H,
(b) hydroxy$C_{1-4}$alkyl,
(c) $C_{1-4}$alkyl, or
(d) $COR^5$;

$R^{11}$ is each independently
(a) H,
b) halogen,
(c) $C_{1-4}$alkyl,
(d) hydroxy,
(e) hydroxy $C_{1-4}$alkyl,
(f) $C_{1-4}$alkoxy,
(g) $CF_3$,
(h) CN,
(i) $COR^5$, or
(j) $S(O)_nCH_3$ wherein n is 0, 1 or 2;

$R^{12}$ is $S(O)_2CH_3$ or $S(O)_2NH_2$.

10. A compound according to claim 1 wherein $R^1$ and $R^2$ are each independently selected from the group consisting of
- (a) H,
- (b) halogen,
- (c) hydroxy,
- (d) $C_{1-4}$alkyl,
- (e) $C_{2-4}$alkenyl,
- (f) $C_{2-4}$alkynyl,
- (g) $C_{1-4}$alkoxy,
- (h) hydroxy $C_{1-4}$alkyl,
- (i) $C_{1-4}$alkylthio, $R^8$ and $R^9$ are each independently
- (a) H,
- (b) hydroxy$C_{1-4}$alkyl,
- (c) $C_{1-4}$alkyl;

$R^{11}$ is
- (a) H,
- (b) halogen,
- (c) $C_{1-4}$alkyl,
- (d) hydroxy,
- (e) hydroxy $C_{1-4}$alkyl,
- (f) $C_{1-4}$alkoxy,
- (g) CN,
- (h) $S(O)_nCH_3$ wherein n is 0, 1 or 2;

$R^{12}$ is $S(O)_2CH_3$ or $S(O)_2NH_2$.

11. A compound according to claim 10 wherein $R^1$ and $R^2$ are each independently selected from the group consisting of
- (a) H,
- (b) $C_{1-4}$alkyl, $R^8$ and $R^9$ are each independently
- (a) H,
- (b) hydroxy$C_{1-4}$alkyl,
- (c) $C_{1-4}$alkyl;

$R^{11}$ is each independently
- (a) H,
- (b) halogen,
- (c) $C_{1-4}$alkyl;

$R^{12}$ is $S(O)_2CH_3$ or $S(O)_2NH_2$.

12. A compound according to claim 1 of Formula Ie'

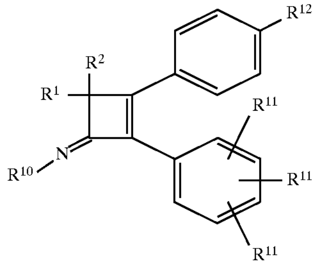

Ie' wherein $R^1$ and $R^2$ are each independently selected from the group consisting of
- (a) H,
- (b) halogen,
- (c) hydroxy,
- (d) $C_{1-4}$alkyl,
- (e) $C_{2-4}$alkenyl,
- (f) $C_{1-4}$alkoxy,
- (g) hydroxy $C_{1-4}$alkyl,
- (h) CN,
- (i) $COR^5$,
- (j) $OCOR^6$,
- (k) $OCONHR^7$, or
- (l) a mono-, di- or tri-substituted phenyl, wherein the substituents are each independently $R^{11}$, or $R^1$ and $R^2$ are joined together with the carbon atom to which they are attached to form a saturated monocyclic ring of 3,4,5 or 6 carbon atoms, $R^5$ is
- (a) H,
- (b) $C_{1-4}$alkyl, or
- (c) $C_{1-4}$alkoxy;

$R^6$ is
- (a) $C_{1-4}$alkyl, or
- (b) $C_{1-4}$alkoxy;

$R^7$ is
- (a) H,
- (b) $C_{1-4}$alkyl, or
- (c) mono-, di- or tri-substituted phenyl, wherein the substituents are each independently $R^{11}$;

$R^{10}$ is
- (a) $C_{1-4}$alkoxy, or
- (b) substituted $C_{1-4}$alkyl or $C_{1-4}$alkoxy, wherein the substituent is a mono-, di- or tri-substituted phenyl or pyridyl and the substituents on the phenyl or pyridyl are $R^{11}$;

$R^{11}$ is each independently
- (a) H,
- (b) halogen,
- (c) $C_{1-4}$alkyl,
- (d) hydroxy,
- (e) hydroxy $C_{1-4}$alkyl,
- (f) $C_{1-4}$alkoxy,
- (g) $CF_3$,
- (h) CN,
- (i) $S(O)_nCH_3$ wherein n is 0, 1 or 2;

$R^{12}$ is $S(O)_2CH_3$ or $S(O)_2NH_2$.

13. A compound according to claim 12 wherein $R^1$ and $R^2$ are each independently selected from the group consisting of
- (a) H,
- (b) halogen,
- (c) hydroxy,
- (d) $C_{1-4}$alkyl,
- (e) $C_{1-4}$alkoxy,
- (f) hydroxy $C_{1-4}$alkyl,
- (g) CN, or
- (i) a mono-, di- or tri-substituted phenyl, wherein the substituents are each independently $R^{11}$, or $R^1$ and $R^2$ are joined together with the carbon atom to which they are attached to form a saturated monocyclic ring of 3,4,5 or 6 carbon atoms, $R^{10}$ is
- (a) $C_{1-4}$alkoxy, or
- (b) substituted $C_{1-4}$alkyl or $C_{1-4}$alkoxy, wherein the substituent is a mono-, di- or tri-substituted phenyl or pyridyl and the substituents on the phenyl or pyridyl are $R^{11}$;

$R^{11}$ is each independently
- (a) H,
- (b) halogen,
- (c) $C_{1-4}$alkyl,
- (d) hydroxy,
- (e) hydroxy $C_{1-4}$alkyl,
- (f) $C_{1-4}$alkoxy,
- (g) $CF_3$, (h) CN, (i) $S(O)_nCH_3$ wherein n is 0, 1 or 2;

$R^{12}$ is $S(O)_2CH_3$ or $S(O)_2NH_2$.

14. A compound according to claim 13 wherein $R^1$ and $R^2$ are each independently selected from the group consisting of (a) H, (b) halogen, (c) hydroxy, (d) $C_{1-4}$alkyl, or (e) a mono-, di- or tri-substituted phenyl, wherein the substituents are each independently $R^{11}$, $R^1$ and $R^2$ are joined together with the carbon atom to which they are attached to form a saturated monocyclic ring of 3,4,5 or 6 carbon atoms, $R^{10}$ is (a) $C_{1-4}$alkoxy, or (b) substituted $C_{1-4}$alkyl or $C_{1-4}$alkoxy, wherein the substituent is a mono-, di- or tri-substituted phenyl or pyridyl and the substituents on the phenyl or pyridyl are $R^{11}$;

$R^{11}$ is each independently (a) H, (b) halogen, (c) $C_{1-4}$alkyl, $R^{12}$ is $S(O)_2CH_3$ or $S(O)_2NH_2$.

15. A compound selected from the group consisting of:

(1) 4,4-Dichloro-3-(4-methylthiophenyl)-2-phenyl-2-cyclobuten-1-one;

(2) 4,4-Dichloro-3-(4-methylsulfonylphenyl)-2-phenyl-2-cyclobuten-1-one;

(3) 4-Chloro-3-(4-methylsulfonylphenyl)-2-phenyl-2-cyclobuten-1-one;

(4) 3-(4-methylsulfonylphenyl)-2-phenyl-2-cyclobuten-1-one (5) 4,4-Dichloro-3-(4-methylsulfonylphenyl)-2-(4-fluorophenyl)-2-cyclobuten-1-one;

(8) 4-Methyl-3-(4-methylsulfonylphenyl)-2,4-diphenyl-2-cyclobuten-1-one;

(9) 3-(4-Methylsulfonylphenyl)-2-phenylspiro[4.6]-2-nonen-1-one;

(10) 3-(4-Methylsulfonylphenyl)-2-phenylspiro[4.5]-2-octen-1-one;

(11) 3-(4-Methylsulfonylphenyl)-4-phenyl-3-cyclobuten-1,2-dione-2-(ethylene acetal);

(12) 3-(4-Methylsulfonylphenyl)-4-phenyl-3-cyclobuten-1,2-dione;

(13) 4-Methoxy-4-methyl-3-(4-methylsulfonylphenyl)-2-phenyl-2-cyclobuten-1-one;

(14) 4-Methoxy-4-butyl-3-(4-methylsulfonylphenyl)-2-phenyl-2-cyclobuten-1-one;

(15) (Z)-Methyl [4-(4-methylsulfonylphenyl)-3-phenyl-3-cyclobuten-2-one-1-ylidene]acetate;

(16) 4,4-Dimethyl-3-(4-methylsulfonylphenyl)-2-phenyl-2-cyclobuten-1-one;

(17) 4,4-Dimethyl-3-(4-methylsulfonylphenyl)-2-(3-fluorophenyl)-2-cyclobuten-1-one;

(18) 4,4-Dimethyl-3-(4-methylsulfonylphenyl)-2-(4-fluorophenyl)-2-cyclobuten-1-one;

(19) 4,4-Dimethyl-3-(4-methylsulfonylphenyl)-2-(3,5-difluorophenyl)-2-cyclobuten-1-one;

(20) 4,4-Dimethyl-3-(4-methylsulfonylphenyl)-2-(3,4-difluorophenyl)-2-cyclobuten-1-one;

(21) 4,4-Dimethyl-3-(4-methylthiophenyl)-2-phenyl-2-cyclobuten-1-one;

(22) 4,4-Dimethyl-3-(4-methylsulfinylphenyl)-2-phenyl-2-cyclobuten-1-one;

(23) 4,4-Dimethyl-3-(4-aminosulfonylphenyl)-2-phenyl-2-cyclobuten-1-one;

(25) 2-(4-methylsulfonylphenyl)-3-phenylspiro[4.6]-2-nonen-1-one;

(26) 2-(4-methylsulfonylphenyl)-3-phenylspiro[4.5]-2-octen-1-one;

(27) 2-(4-Methylsulfonylphenyl)-3-phenylspiro[4.4]-2-hepten-1-one;

(28) 4,4-dimethyl-2-(4-methylsulfonylphenyl)-3-(3-fluorophenyl)-2-cyclobuten-1-one;

(29)4,4-dimethyl-2-(4-methylsulfonylphenyl)-3-(4-fluorophenyl)-2-cyclobuten-1-one; (30)4,4-dimethyl-2-(4-methylsulfonylphenyl)-3-phenyl-2-cyclobuten-1-one;

(31)4,4-dimethyl-2-(4-methylthiophenyl)-3-phenyl-2-cyclobuten-1-one;

(32) 4,4-Dimethyl-2-(4-methylsulfinylphenyl)-3-phenyl-2-cyclobuten-1-one;

(33) (trans)-2,2-Dimethyl-3,4-bis(4-methylthiophenyl)-1-cyclobutanone;

(34) 4-Methyl-2-(4-methylsulfonylphenyl)-3-phenyl-2-cyclobuten-1-one;

(35) 4-Isopropyl-2-(4-methylsulfonylphenyl)-3-phenyl-2-cyclobuten-1-one;

(36) 4,4-Dichloro-3-methylene-1-(4-methylsulfonylphenyl)-2-phenyl-1-cyclobutene;

(37) Ethyl [4,4-dichloro-3-(4-methylsulfonylphenyl)-2-phenyl-2-cyclobuten-1-ylidene]acetate;

(38) [4,4-Dichloro-3-(4-methylsulfonylphenyl)-2-phenyl-2-cyclobuten-1-ylidene]ethanol;

(39) 3-Methylene-1-(4-methylsulfonylphenyl)-2-phenyl-1-cyclobutene;

(40) (E)-Ethyl [3-(4-methylsulfonylphenyl)-2-phenyl-2-cyclobuten-1-ylidene]acetate;

(41) (Z)-Ethyl [3-(4-methylsulfonylphenyl)-2-phenyl-2-cyclobuten-1-ylidene]acetate;

(42) (Z) and (E)-[3-(4-methylsulfonylphenyl)-2-phenyl-2-cyclobuten-1-ylidene]-2-propanol;

(43) (Z) and (E)-[3-(4-methylsulfonylphenyl)-2-phenyl-2-cyclobuten-1-ylidene]-2-propanol;

(44) 4,4-Dimethyl-3-methylene-1-(4-methylsulfonylphenyl)-2-phenyl-1-cyclobutene;

(45) 4,4-Dimethyl-3-(4-methylsulfonylphenyl)-2-phenyl-2-cyclobuten-1-one oxime;

(46) 4,4-Dimethyl-3-(4-methylsulfonylphenyl)-2-phenyl-2-cyclobuten-1-one t-butyloxime;

(47) 4,4-Dimethyl-3-(4-methylsulfonylphenyl)-2-phenyl-2-cyclobuten-1-one methyloxime;

(48) 4,4-Dimethyl-3-(4-methylsulfonylphenyl)-2-phenyl-2-cyclobuten-1-one benzyloxime;

(49) 1-N-Benzylimine-4,4-dimethyl-3-(4-methylsulfonylphenyl)-2-phenyl-2-cyclobutene;

(50) 4,4-Dimethyl-3-(4-methylsulfonylphenyl)-2-phenyl-2-cyclobuten-1-one 3-picolyloxime;

(51) 4,4-Dimethyl-3-(4-methylsulfonylphenyl)-2-phenyl-2-cyclobuten-1-one 2-picolyloxime;

(52) 4,4-Dimethyl-3-(4-methylsulfonylphenyl)-2-phenyl-2-cyclobuten-1-one (3-carbomethoxy)benzyl oxime;

(53) 4,4-Dimethyl-3-(4-methylsulfonylphenyl)-2-phenyl-2-cyclobuten-1- one (3-carboxy)benzyl oxime;

(54) 3-(4-Methylsulfonylphenyl)-2-phenyl-2-cyclobuten-1-one oxime;

(55) 3-(4-Methylsulfonylphenyl)-2-phenyl-2-cyclobuten-1-one t-butyloxime;

(56) 4,4-Dimethyl-3-(4-methylsulfonylphenyl)-2-phenyl-2-cyclobuten-1-one methyloxime;

(57) 3-(4-Methylsulfonylphenyl)-2-phenyl-2-cyclobuten-1-one benzyloxime;

(58) 4,4-Dimethyl-2-(4-methylsulfonylphenyl)-3-phenyl-2-cyclobuten-1-one t-butyloximes;

(59) 4,4-Dimethyl-2-(4-methylsulfonylphenyl)-3-phenyl-2-cyclobuten-1-one benzyloxime;

(60) 1-(4-Methylsulfonylphenyl)-2-phenyl-1-cyclobutene;

(61) 1,4,4-Trimethyl-3-(4-methylsulfonylphenyl)-2-phenyl-2-cyclobuten-1-ol;

(62) 4,4-Dimethyl-3-(4-methylsulfonylphenyl)-2-phenyl-2-cyclobuten-1-ol;

(63) 4,4-Dimethyl-1-methoxy-3-(4-methylsulfonylphenyl)-2-phenyl-2-cyclobutene;

(64) 4,4-Dimethyl-1-acetoxy-3-(4-methylsulfonylphenyl)-2-phenyl-2-cyclobutene;

(65) 4,4-Dimethyl-1-pivaloxy-3-(4-methylsulfonylphenyl)-2-phenyl-2-cyclobutene;

(66) 4,4-Dimethyl-1-fluoro-3-(4-methylsulfonylphenyl)-2-phenyl-2-cyclobutene;

(67) 4,4-Dimethyl-3-(4-methylsulfonylphenyl)-2-phenyl-2-cyclobuten-1-ol N-phenylcarbamate;

(68) 4,4-Dimethyl-3-(4-methylsulfonylphenyl)-2-phenyl-2-cyclobuten-1-one (ethylenedithioacetal);

(69) 4,4-Dimethyl-2-(4-methylsulfonylphenyl)-3-phenyl-2-cyclobuten-1-ol;

(70) 4,4-Dimethyl-1-methoxy-2-(4-methylsulfonylphenyl)-3-phenyl-2-cyclobutene; and

(71) 4,4-Dimethyl-1-acetoxy-2-(4-methylsulfonylphenyl)-3-phenyl-2-cyclobutene.

16. A pharmaceutical composition for treating an inflammatory disease susceptable to treatment with an non-steroidal anti-inflammatory agent comprising:

a non-toxic therapeutically effective amount of a compound according to claim 1 and a pharmaceutically acceptable carrier.

17. A pharmaceutical composition for treating cyclooxygenase mediated diseases advantageously treated by an active agent that selectively inhibits COX-2 in preference to COX-1 comprising:

a non-toxic therapeutically effective amount of a compound according to claim 1 and a pharmaceutically acceptable carrier.

18. A method of treating an inflammatory disease susceptable to treatment with an non-steroidal anti-inflammatory agent comprising:

administration to a patient in need of such treatment of a non-toxic therapeutically effective amount of a compound according to claim 1 and a pharmaceutically acceptable carrier.

19. A method of treating cyclooxygenase mediated diseases advantageously treated by an active agent that selectively inhibits COX-2 in preference to COX-1 comprising:

administration to a patient in need of such treatment of a non-toxic therapeutically effective amount of a compound according to claim 1.

20. A compound of formula I:

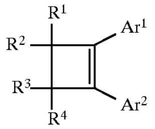

I or a pharmaceutically acceptable salt thereof, wherein:

$R^1$, $R^2$,$R^3$ and $R^4$ are each independently selected from the group consisting of:

(a) H, (b) halogen, (c) hydroxy, (d) $C_{1-6}$alkyl, (e) $C_{2-6}$alkenyl, (f) $C_{2-6}$alkynyl, (g) $C_{1-6}$alkoxy, (h) hydroxy $C_{1-6}$alkyl, (i) $C_{1-6}$alkylthio, (j) CN, (k) $COR^5$, (l) $OCOR^6$, (m) $OCONHR^7$ and (n) a mono-, di- or tri-substituted phenyl, wherein the substituents are each independently $R^{11}$;

or $R^1$ and $R^2$ or $R^3$ and $R^4$ are joined together with the carbon atom to which they are attached to form C═O, or $R^1$ and $R^2$ or $R^3$ and $R^4$ are joined together with the carbon atom to which they are attached to form C═S, or $R^1$ and $R^2$ or $R^3$ and $R^4$ are joined together with the carbon atom to which they are attached to form $C{=}CR^8R^9$, or $R^1$ and $R^2$ or $R^3$ and $R^4$ are joined together with the carbon atom to which they are attached to form $C{=}NR^{10}$, or $R^1$ and $R^2$ or $R^3$ and $R^4$ are joined together with the carbon atom to which they are attached to form a saturated monocyclic ring of 3,4,5,6 or 7 carbon atoms;

$Ar^1$ is mono-substituted phenyl or naphthyl wherein the substituent is $R^{12}$;

$Ar^2$ is mono-, di- or tri-substituted phenyl, wherein the substituents are each independently $R^{11}$;

$R^5$ is selected from the group consisting of:

(a) H, (b) $C_{1-6}$alkyl and (c) $C_{1-6}$alkoxy;

$R^6$ is selected from the group consisting of:

(a) $C_{1-6}$alkyl, (b) $C_{1-6}$alkoxy and (c) mono-, di- or tri-substituted phenyl, wherein the substituents are each independently $R^{11}$;

$R^7$ is selected from the group consisting of:

(a) H, (b) $C_{1-6}$alkyl and (c) mono-, di- or tri-substituted phenyl, wherein the substituents are each independently $R^{11}$;

$R^8$ and $R^9$ are each independently selected from the group consisting of:

(a) H, (b) hydroxy $C_{1-6}$alkyl, (c) $C_{1-6}$alkyl, (d) CN and (e) $COR^5$;

$R^{10}$ is selected from the group consisting of:

(a) hydroxy, (b) $C_{1-6}$alkoxy, (c) $C_{1-6}$alkyl and (d) substituted $C_{1-6}$alkyl or $C_{1-6}$alkoxy, wherein the substituent is a mono-, di- or tri-substituted phenyl and the substituent or substituents on the phenyl are $R^{11}$;

$R^{11}$ is selected from the group consisting of:

(a) H, (b) halogen, (c) $C_{16}$alkyl, (d) hydroxy, (e) hydroxy $C_{1-6}$alkyl, (f) $C_{1-6}$alkoxy, (g) $CF_3$, (h) CN, (i) $COR^5$and (j) $S(O)_nR^{13}$ wherein n is 0, 1 or 2;

$R^{12}$ is $S(O)_nR^{13}$ or $S(O)_2NHR^{14}$;

$R^{13}$ is $C_{1-6}$alkyl, and $R^{14}$ is H or $C_{1-6}$alkyl.

21. A compound of formula I:

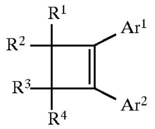

I or a pharmaceutically acceptable salt thereof, wherein $R^1$ and $R^2$ are methyl;

$R^3$ and $R^4$ are joined together with the carbon atom to which they are attached to form C═O;

$Ar^1$ is phenyl mono-substituted at the 4-position wherein the substituent is $R^{12}$;

$R^{12}$ is $SO_2Me$; and $Ar^2$ is phenyl.

* * * * *